US006468781B1

(12) United States Patent
Hanson et al.

(10) Patent No.: US 6,468,781 B1
(45) Date of Patent: Oct. 22, 2002

(54) STEREOSELECTIVE REDUCTIVE AMINATION OF KETONES

(75) Inventors: Ronald Hanson, Morris Plains; Mary Jo Donovan, North Brunswick; Steven Goldberg, Gillette, all of NJ (US); Paul A. Jass, Charles City, IA (US); Wen-Sen Li, Holmdel, NJ (US); Ramesh Patel, Bridgewater, NJ (US); Keith Ramig, Orange, NJ (US); Laszlo J. Szarka, East Brunswick, NJ (US); John J. Venit, North Brunswick, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/510,925

(22) Filed: Feb. 22, 2000

Related U.S. Application Data

(62) Division of application No. 09/350,428, filed on Jul. 8, 1999, now Pat. No. 6,140,088.

(51) Int. Cl.$^7$ .......................... C12P 21/06; C12N 9/00; C12N 9/02; C12N 1/12; C12N 1/18
(52) U.S. Cl. ................ 435/255.1; 435/69.2; 435/183; 435/189; 435/252.1
(58) Field of Search ............................. 435/69.1, 183, 435/254.11, 106, 189, 255.1, 254.2

(56) References Cited

U.S. PATENT DOCUMENTS

| | | | |
|---|---|---|---|
| 4,970,157 A | * | 11/1990 | Hibino et al. |
| 5,015,582 A | * | 5/1991 | Hibino et al. |
| 5,508,272 A | | 4/1996 | Robl |
| 5,965,389 A | * | 10/1999 | Raymond et al. |

FOREIGN PATENT DOCUMENTS

| WO | WO98/48040 | 10/1998 |
|---|---|---|

OTHER PUBLICATIONS

Allen et al. Isolation and overexpression of the gene encoding NAD_dependent formate dehydrogenase from the methylotrophic yeast *C.methylica*, May, 1995.*
Sakai et al. J.Bacteriol. vol. 179–4480–4485, Jul. 1997.*
Robl, J.A., et al., J. Med. Chem. vol. 40, May 1997 pp. 1570–1577.
Rumbero, A., et al., Bioorg. Med. Chem. vol. 3, No. 9, (1995), pp. 1237–1240.
Galkin, A., et al., Appl. Environ. Microbiol. vol. 63, No. 12, Dec. 1997, pp. 4651–4656.
Hanson, R.L. et al., Bioorg. Chemistry, vol. 18, (1990), pp. 116–130.
Hanson, R.L. et al. Bioorg. Med. Chem. vol. 7, (1999), pp. 2247–2252.
Singh, J., et al., Org. Prep. Proced. Int., vol. 21, No. 4, (1989), pp. 501–504.
Schutte, H., et al., Eur. J. Biochem., vol. 62, (1976), pp. 151–160.
Couderc, R., et al., Agric. Biol. Chem. vol. 44, No. 10, Jan. 1980, pp. 2279–2289
Hou, C.T., et al., Arch. Biochem. Biophys., vol. 216, No. 1 1982, pp. 296–305.
Allais, J.J., et al., Agric. Biol. Chem., vol. 47, No. 11, Apr. 1983, pp. 2547–2554.
Ohshima, T., et al., J. Bacteriol., vol. 173, No. 13, Jul. 1991, pp. 3943–3948.
Takada, H., et al., J. Biochem., vol. 109, 1991, pp. 371–376.
Ohshima, T., et al., Anal. Lett., vol. 21, No. 12, 1998, pp. 2205–2215.
Shaked, Z., et al., J. Am. Chem. Soc., vol. 102, 1980, pp. 7104–7105.
Kula, M.R., et al., Methods in Enzymology, vol. 136, (1987), pp. 9–21.
Hanson, R. et al., Enzyme & Microbial Technology vol. 26, (2000), pp. 348–358.

* cited by examiner

*Primary Examiner*—Ponnathapu Achutamurthy
*Assistant Examiner*—Manjunath N. Rao
(74) *Attorney, Agent, or Firm*—Audrey F. Sher

(57) ABSTRACT

Processes for stereoselective enzymatic conversion of certain keto carboxylic acid derivatives to form the corresponding alkylamino acid compounds are described. The invention also concerns an engineered yeast host cell containing recombinant nucleic acid capable of expressing a phenylalanine dehydrogenase, as well as an engineered host cell containing recombinant nucleic acid capable of expressing a phenylalanine dehydrogenase enzyme and nucleic acid capable of expressing a formate dehydrogenase enzyme.

14 Claims, 6 Drawing Sheets

STEREOSELECTIVE REDUCTIVE AMINATION OF KETONES

CROSS-REFERENCE TO RELATED APPLICATIONS

This is a divisional application of Ser. No. 09/350,428 filed Jul. 8, 1999 now U.S. Pat. No. 6,140,088, Oct. 31, 2000, which is related to provisional application Ser. No. 60/092,935 filed Jul. 15, 1998.

FIELD OF INVENTION

The present invention concerns a stereoselective enzymatic reductive amination process.

BACKGROUND OF THE INVENTION

Rob1 in U.S. Pat. No. 5,508,272 disclose compounds of the formula

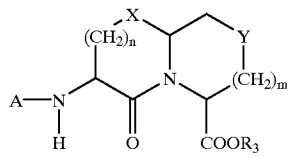

wherein A is

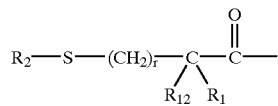

as possessing neutral endopeptidase and angiotensin converting enzyme inhibition activity. Among these compounds is [4S-[4∀(R*), 7∀, 10a∃]]-octahydro-4-[(2-mercapto-1-oxo-3-phenylpropyl)amino]-5-oxo-7H-pyrido[2,1-b][1,3]thiazepine-7-carboxylic acid which is currently undergoing clinical evaluation.

Rob1 discloses that the amino lactam portion of this compound, i.e., the intermediate

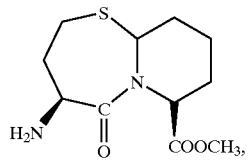

can be prepared by coupling an alkyl ester compound such as (S)-2-amino-6,6-dimethoxyhexanoic acid methyl ester with the N-protected amino acid

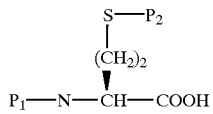

wherein $P_1$ is an amino protecting group and $P_2$ is a sulfur protecting group to give the dipeptide of the formula

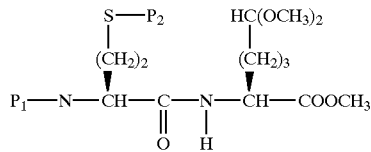

Removal of the $P_2$ protecting group, followed by acid catalyzed cyclization, and removal of the $P_1$ protecting group gives [4S-(4∀, 7∀, 10a∃)]-octahydro-4-amino-5-oxo-7H-pyrido[2,1-b][1,3]thiazepine-7-carboxylic acid, methyl ester.

Rob1 discloses preparing (S)-2-amino-6,6-dialkoxyhexanoic acid, alkyl ester, such as (S)-2-amino-6,6-dimethoxyhexanoic acid, methyl ester, by converting N-protected L-γ-hydroxynorleucine to its methyl ester, oxidizing to a corresponding aldehyde, such as of the formula

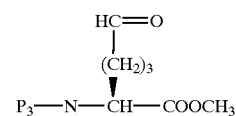

then reacting with trimethyl orthoformate in the presence of a strong acid catalyst, and removing the $P_3$ protecting group

SUMMARY OF THE INVENTION

The present invention provides a process for the stereoselective enzymatic conversion of certain keto carboxylic acid derivatives to form the corresponding alkylamino acid compounds. The amino compounds prepared by the enzymatic process of the invention can be conveniently converted to the corresponding (S)-2-amino-6,6-dialkoxyhexanoic acid, alkyl ester or stable salts of such compounds such as phosphate, oxalate or bis salt with a compound such as (N-(trifluoroacetyl)-L-homocysteine, (1→1')-disulfide.

More specifically, the present invention is directed to a process for preparing an alkylamino acid compound of the formula (formula I)

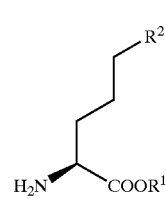

wherein $R^1$ is hydrogen or a monovalent cation or a $C_1$–$C_{18}$ alkyl (preferably $C_1$–$C_{10}$ alkyl, more preferably lower alkyl), $R^2$ is a moiety of the formula

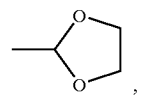

a moiety of the formula

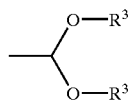

wherein each $R^3$ is a $C_1$–$C_{18}$ alkyl (preferably $C_1$–$C_{10}$ alkyl, more preferably lower alkyl); or a moiety of the formula

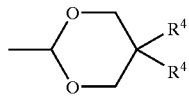

wherein each $R^4$ is H or $R^3$ comprising contacting an alkylketo compound of the formula (formula II)

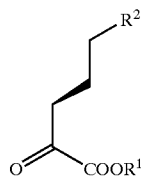

wherein $R^2$ is as defined above, and $R^1$ is as defined above, with an amino acid dehydrogenase in the presence of ammonia and a co-factor under conditions suitable for formation of the compound of formula I.

The present invention also concerns an engineered yeast host cell containing recombinant nucleic acid capable of expressing a phenylalanine dehydrogenase enzyme and endogenous or recombinant nucleic acid capable of expressing a formate dehydrogenase enzyme.

DETAILED DESCRIPTION OF THE INVENTION

Figure 1:
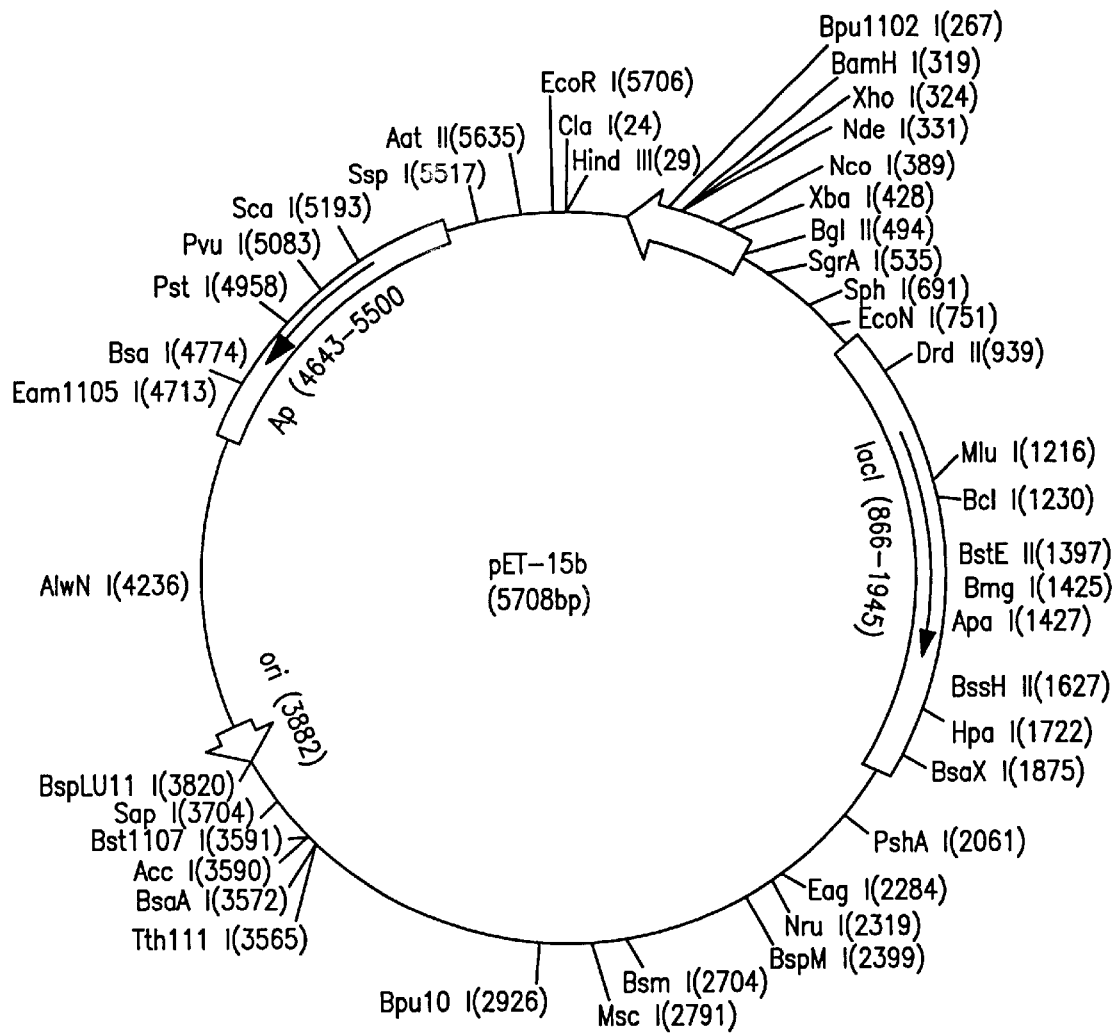
FIG. 1. Plasmid pET-15b. The sequence is numbered by the pBR322 convention. Sequence landmarks include T7 promoter at 453–469. T7 transcription start at 452; His Tag coding sequence at 362–380. T7 terminator at 213–259; pBR322 origin at 3882; and bla coding sequence at 4643–5500.

In the above formulas the monovalent cation can be, for example, lithium, potassium, sodium, ammonium, and the like. It is preferred that $R^1$ is hydrogen, ammonium, lithium, or potassium; and that $R^2$ is a dioxolane moiety of the formula

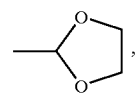

It is also preferred that $R^3$ is lower alkyl, especially methyl.

The most preferred reductive amination process of the invention comprises the conversion of 5-(1,3-dioxolan-2-yl)-2-oxo-pentanoic acid to 5-(1,3-dioxolan-2-yl)-2S-amino-pentanoic acid (L-allysine ethylene acetal) by reductive amination which is depicted below:

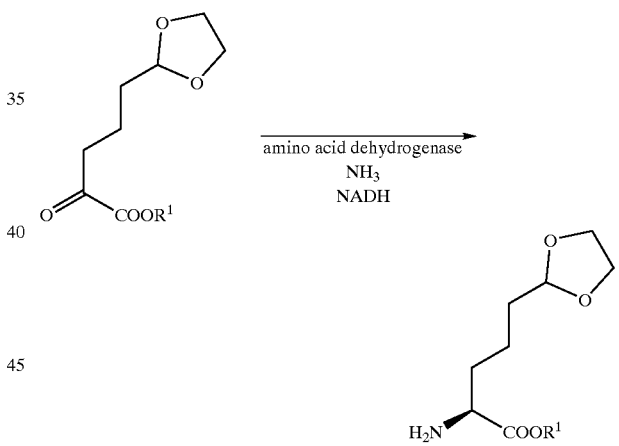

wherein $R^1$ is hydrogen or lithium.

The term "alkyl" or "alk" as used herein alone or as a part of another group, denotes such optionally substituted, but preferably unsubstituted, straight and branched chain saturated hydrocarbon groups, preferably having 1 to 10 carbons in the normal chain. Exemplary unsubstituted such groups include methyl, ethyl, propyl, isopropyl, n-butyl, iso-butyl, t-butyl, pentyl, hexyl, isohexyl, heptyl, 4,4-dimethyl, pentyl, octyl, 2,2,4-trimethylpentyl, nonyl, decyl and the like. The alkyl groups may be substituted by appropriate substituents providing compounds suitable for use in the present invention. Exemplary substituents of the alkyl group include one or more, preferably three or fewer, chloro groups, bromo groups, or iodo groups.

The term "lower alkyl" as used herein denotes alkyl groups having 1 to 3 carbon atoms.

The reductive amination process of the present invention has the advantage of producing an enantiospecific result.

The process primarily yields the S enantiomer rather than a racemic mixture of preferred and unpreferred enantiomers. Additional advantages of particular embodiments include, for example, a single step enantiospecific reduction compared with multi-step chemical synthesis. Also, particularly when the reduction is catalyzed at about 40° C. and ambient pressure, one obtains high conversion from the ketone compound to the desired enantiomer of the corresponding amine compound, and high enantiomeric purity of the amine compound.

For the enzymatic conversion process, if $R^1$ is a monovalent cation, such as Li, typically the isolation procedure involves lowering the pH which converts the cation to H.

The amino acid dehydrogenase employed in the present invention may be any amino acid dehydrogenase capable of catalyzing the stereoselective enzymatic reductive amination described herein. Enzymatic or microbial materials as the source of the enzyme may be employed in the free state or immobilized on a support such as by physical adsorption or entrapment.

Suitable enzymes, regardless of origin or purity, are those enzymes referred to as amino acid dehydrogenases. The enzyme employed may, for example, be an enzyme isolated from a microorganism such as by homogenizing cell suspensions, followed by disintegration, centrifugation, DEAE-cellulose chromatography, ammonium sulfate fractionation, chromatography using gel filtration media such as Sephacryl (crosslinked co-polymer of allyl dextran and N,N'-methylene bisacrylamide) chromatography, and ion exchange chromatography such as Mono-Q (anion exchanger which binds negatively charged biomolecules through quaternary amine groups) chromatography.

Alternatively, the reductive amination process of the invention may use intact cells or cell extracts as a source of the enzyme. With respect to the use of microorganisms, the method of the present invention may be carried out using any suitable microbial materials capable of catalyzing the stereoselective enzymatic reduction described herein. For example, the cells may be used in the form of intact wet cells or dried cells such as lyophilized, spray-dried or heat-dried cells, or in the form of treated cell material such as ruptured cells or cell extracts. Suitable microorganisms include genera from bacteria, yeasts and fungi, for example, Bacillus sp. such as *B. subtilis,* Sporosarcina sp., Thermoactinomyces sp. such as *T. intermedius,* and the like.

The use of genetically engineered organisms is also contemplated. The host cell may be any cell, e.g., *Escherichia coli, Pichia pastoris,* and the like, modified to contain a gene or genes for expressing one or more amino acid dehydrogenases capable of catalysis as described herein.

As explained in more detail hereinafter, certain preferred engineered organisms of the invention also express a second enzyme that regenerates the co-factor (such as formate dehydrogenase). The nucleic acid encoding this second enyzme can be either endogenous or genetically engineered into the cell via recombinant technology.

It is particularly preferred to employ microorganisms of the genus Pichia, particularly the species *Pichia pastoris,* especially the strains *Pichia pastoris* ATCC 74408 and *Pichia pastoris* ATCC 74433. Another preferred organism is *E. coli* ATCC 98374. The term "ATCC" as used herein refers to the accession number of the American Type Culture Collection. Patent Depository. 10801 University Boulevard, Manassas, Va. 20110-2209, the depository for the organism referred to. *Pichia pastoris* ATCC 74408 was deposited with the ATCC on Mar. 26, 1997 under the provisions of the Budapest Treaty. *Pichia pastoris* ATCC 74433 was deposited with the ATCC on Feb. 13, 1998 under the provisions of the Budapest Treaty, and *E. coli* ATCC 98374 was deposited with the ATCC on Mar. 26, 1997 under the provisions of the Budapest Treaty. It is also particularly preferred to employ cell extracts or isolated enzymes from these organisms (microorganisms) in the present invention.

The stereoselective enzymatic reduction method of the present invention may be carried out subsequent to the fermentation of the microorganism employed (two-stage fermentation and reduction), or concurrently therewith, that is, in the latter case, by in situ fermentation and reduction (single-stage fermentation and reduction). In the single-stage process, the microorganisms may be grown in an appropriate medium until sufficient growth of the microorganisms is attained. A compound of Formula II may then be added to the microbial cultures and the stereoselective enzymatic reduction continued with the fermentation, preferably until complete conversion is obtained.

In the two-stage process, the microorganisms may, in the first stage, be grown in an appropriate medium for fermentation until exhibiting the desired enzymatic (i.e., reductive amination) activity. Subsequently, the cells may be harvested by centrifugation and microbial cell suspensions prepared by suspending harvested cells in an appropriate buffered solution. Buffers such as Tris-HCl, phosphate, sodium acetate and the like may be used. Water may also be used to prepare suspensions of microbial cells. In the second stage, the compound of Formula II may be mixed with the microbial cell suspensions, and the stereoselective enzymatic reduction of the compound catalyzed by the microbial cell suspension. The reduction is preferably conducted until all or nearly all of the compound of Formula II is stereoselectively reduced.

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and trace elements. Inducers may also be added. The term "inducer", as used herein, includes any compound enhancing formation of the desired enzymatic reductive amination activity within the microbial cell, such as those compounds containing keto groups. Formula I compounds may be added as inducers during growth of the microorganism. For genetically engineered yeast and bacterial cultures methanol and isopropyl beta galactoside (IPTG), respectively, are good inducers.

Carbon sources may include sugars such as maltose, lactose, glucose, fructose, glycerol, sorbitol, sucrose, starch, mannitol, propylene glycol, and the like; organic acids such as sodium formate, sodium acetate, sodium citrate, and the like; amino acids such as sodium glutamate and the like; and alcohols such as methanol, ethanol, propanol and the like.

Nitrogen sources may include N–Z amine A, corn steep liquor, soy bean meal, beef extracts, yeast extracts, yeastamin, molasses, baker's yeast, tryptone, nutrisoy, peptone, sodium nitrate, ammonium sulfate and the like.

Trace elements may include phosphates and magnesium, manganese, calcium, cobalt, nickel, iron, sodium and potassium salts.

The medium employed may include more than one carbon or nitrogen source or other nutrient.

A preferred medium for Thermoactinomyces sp is an aqueous medium having the following components (in weight %):

| Component | |
|---|---|
| L-phenylalanine | 0.5% |
| NZ Amine A | 2% |
| Yeast Extract | 0.5% |
| K$_2$HPO$_4$ | 0.2% |
| NaH$_2$PO$_4$ | 0.1% |
| MgSO$_4$ H$_2$O | 0.02% |
| antifoam. e.g., SAG5693 | 0.02% |
| pH 6.5–6.9 | |

A preferred medium for *E. coli* is an aqueous medium having the following components (in weight %):

| Component | |
|---|---|
| NZ Amine A | 1% |
| Yeastamin | 2% |
| Glycerol | 2% |
| Na$_2$HPO$_4$ | 0.6% |
| K$_2$HPO$_4$ | 0.3% |
| (NH$_4$)$_2$SO$_4$ | 0.125% |
| Propylene glycol | 0.05% |
| MgSO$_4$7H$_2$O | 0.0246% |
| Kanamycin | 0.005% |
| isopropyl β-D-thiogalactoside | 0.00238% |
| pH 7.0–7.2 | |

Preferred media for Yeast is an aqueous medium having the following components (in weight %):

| Component | |
|---|---|
| Yeast nitrogen base without amino acids | 1.34% |
| Peptone | 2.0% |
| Yeast extract | 1.0% |
| Glycerol | 1.0% |
| Methanol | 0.5% |
| K2HPO4 | 0.282% |
| KH2PO4 | 1.14% |
| Biotin | 4 × 10$^{-5}$% |
| Antifoam i.e A289 | 0.01% |
| pH 6.0 | |

During growth of yeast on medium 1, the methanol concentration was maintained at about 0.5% by methanol feed as required.

| Component | |
|---|---|
| Peptone | 2.0% |
| Yeast extract | 1.0% |
| Glucose | 2.0% |
| Antifoam A289 | 0.01% |
| pH 6.0 | |

The pH of the medium is preferably adjusted to about 6 to 8, depending upon the particular medium, sterilized, e.g., at a temperature of 121° C. for 30 minutes, and then adjusted to a desirable pH, after sterilization.

The process of the present invention is performed under conditions suitable for forming the desired compound of Formula I. The pH of the medium is preferably maintained between about 4 to 10, more preferably between about 6 and 8, during the growth of microorganisms. During the stereoselective reduction process, whether performed with enzymes or microorganisms, the pH is maintained between about 7 and 9.5, preferably about 8.

Temperature is a measure of the heat energy available for the stereoselective reduction process, and should be maintained to ensure that there is sufficient energy available for this process. A suitable temperature range for the process of the invention is from about 15° C. to about 60° C. A preferred temperature range is from about 25° to about 40° C.

Pressure is not known to be critical to practice of the invention and for convenience about atmospheric pressure is typically employed.

When growing microorganisms, the process of the invention is preferably carried out under aerobic conditions. The agitation and aeration of the reaction mixture affects the amount of oxygen available during the fermentation process and the stereoselective reduction process which may be conducted, for example, in shake-flask cultures or fermentor tanks during growth of microorganisms in a single-stage or two-stage process. The agitation range from 50 to 500 RPM is preferable, with 50 to 100 RPM being most preferred. Aeration of about 0.1 to 10 volumes of air per volume of media per minute (10.1 to 10 v/v/m) is preferred, with aeration of about 5 volumes of air per volume of media per minute (5 v/v/m) being most preferred.

If the reduction process is performed in a second stage after growth of the microorganisms, oxygen is not known to be required and may be detrimental.

Complete conversion of the compound of Formula II may take, for example, from about 4 to 48 hours, preferably about 12 to 30 hours, measured from the time of initially treating the compound of Formula II with a microorganism or enzyme as described herein.

The stereoselective enzymatic reduction method of the present invention is carried out using a co-factor. The co-factor serves as a mediator for reduction of the keto acid. The amount of co-factor is usually about 0.05 to about 2 mM, preferably about 0.5 to about 1 mM. Co-factors useful in the present invention are nicotinamide adenine dinucleotide (NAD), reduced NAD (NADH), nicotinamide adenine dinucleotide phosphate (NADP), and reduced NADP (NADPH). Most preferred is NADH. The use of a cofactor is required when an isolated enzyme is employed. NADH, for example, may be regenerated and reused. Regenerating the co-factor in situ is preferred. A preferred means for regeneration is the use of a second type of enzyme that regenerate the co-factor, such as formate dehydrogenase (FDH), glucose dehydrogenase, alcohol dehydrogenase, and the like. Suitable hydrogen donors include molecular hydrogen glucose, ethanol, or a formate (e.g., an alkali metal or ammonium formate). Chemical reduction (e.g., use of dithionite) or an electrochemical reduction in the presence of a viologen, for example methyl viologen, also can be used. In a preferred embodiment, NAD produced during the reaction is preferably recycled to NADH by the oxidation of formate to carbon dioxide using FDH or by oxidation of glucose to gluconic acid using glucose dehydrogenase. In a preferred embodiment a single host cell strain is used as a source of both PDH and FDH. In an especially preferred embodiment a recombinant or engineered host cell is used as both the source of the amino acid dehydrogenase, especially PDH, and as a source of the FDH. It has been unexpectedly discovered that a preferred organism for use in the present invention, i.e., *Pichia pastoris*, ATCC 74408 not only is engineered to express recombinant PDH, but also that the level of endogenous FDH activity is increased as well.

Another preferred organism for use in the present invention, i.e., *Pichia pistoris* ATCC 74433 is engineered to express both recombinant PDH and recombinant FDH.

It is preferred to employ an aqueous liquid as the reaction medium, although an organic liquid, or a miscible or immiscible (biphasic) organic/aqueous liquid mixture may also be employed.

It is preferred to employ 0.1 to 25 weight % of the compound of Formula II starting material based on the combined weight of the compound and reaction medium. The amount of enzyme or microorganism employed relative to the starting material is selected to allow catalysis of the stereoselective enzymatic reduction of the present invention.

The products of the stereoselective reduction process of the present invention may be isolated and purified, if desired, by known methodologies such as by extraction, distillation, crystallization, column chromatography, and the like.

A preferred method for separating the desired compound of Formula I from the remaining compounds of the reaction medium is concentration by removal of water, then addition of methanol to crystallize out the amino acid.

Preferred amino acid dehydrogenases useful herein are selected from those amino acid dehydrogenases active with the above-described ketone of formula II. Such amino acid dehydrogenases include alanine dehydrogenase, phenylalanine dehydrogenase, leucine dehydrogenase, glutamate dehydrogenase, valine dehydrogenase, and the like. The present invention also contemplates use of two or more amino acid dehydrogenases, particularly when using whole cells or crude extracts. The amino acid dehydrogenases useful in the present invention are typically from a variety of plant, animal, and microbial origins. Alternatively, the enzymes useful in the present invention may be obtained by synthetic means, i.e., chemical synthesis of the polypeptide from its component amino acids, by methods known to those of ordinary skill in the art. For example, the solid phase procedure described in Houghton et al., Proc. Natl. Acad. Sci. 82, 5131–5135 (1985) may be employed. The enzymes may be obtained by production in prokaryotic or eukaryotic host cells expressing a DNA sequence coding for the desired enzyme (endogenous or recombinant), or by in vitro translation of the mRNA encoded by a DNA sequence coding for all or part of the desired enzyme. Techniques for the production of polypeptides by these means are known in the art, and are described herein. Specific examples of enzymes useful herein include, but are not limited to, beef liver glutamate dehydrogenase, alanine dehydrogenase from *Bacillus subtilis,* phenylalanine dehydrogenase from Sporosarcina species, leucine dehydrogenase from *Bacillus sphaericus* ATCC 4525, extract from *Thermoactinomyces intermedius* ATCC 33205 (source of phenylalanine, alanine, and leucine dehydrogenases) and the like. A preferred amino acid dehydrogenase is phenylalanine dehydrogenase (PDH).

The process of the invention requires ammonia. Ammonia is needed because it supplies the amino group for the amino acid compound (i.e., the compound of formula I). Sources of ammonia include $NH_4OH$, urea plus urease, and $HCOONH_4$. The amount of ammonia is typically equimolar or greater than the amount of keto acid compound (i.e., compound of formula II).

Conditions for the enzymatic reductive amination process can vary widely depending on the type of enzyme employed. For example, for the Thermoactinomyces/formate dehydrogenase combination, a temperature of about 35° C. to about 45° C., preferably about 40° C. for a reaction time of about 12 to about 48 hours, preferably about 25 hours, is typically adequate.

The process of the present invention results in high yield of the compound of formula I. A typical yield is greater than about 80%, preferably greater than about 90%, more preferably greater than about 95%, and most preferably about 99%. The present process also results in excellent optical purity, i.e., production of the desired S enantiomers relative to the undesired R enantiomers. Typical optical purity is greater than about 95%, preferably greater than about 99%.

The compounds produced by the reductive amination process of the present invention, such as the L-allysine ethylene acetals, can be readily converted to the ester derivatives disclosed in U.S. Pat. No. 5,508,272, the disclosure of which is incorporated herein by reference in its entirety. The ester derivatives are building blocks to prepare vasopeptidase inhibitors which inhibit both angiotensin converting enzyme (ACE) and neutral endoprotease (NEP) for treatment of cardiovascular diseases as disclosed in U.S. Pat. No. 5,508,272. Therefore, the present invention also includes the optional step of converting the dioxolane acetal-containing compounds of formula I to their corresponding ester derivative. More specifically, the optional esterification additional step comprises exchanging the dioxolane acetal moiety, i.e., wherein $R^2$ is

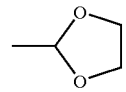

if present, or the moiety

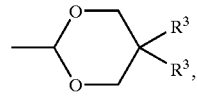

if present, or the moiety

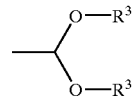

with a dialkoxy acetal and converting the carboxylic acid (if present) to the alkyl ester resulting in the desired compound. (S)-2-amino-6,6-dialkoxyhexanoic acid, alkyl ester. This can be achieved by reacting compound I with thionyl chloride in a suitable solvent such as methanol or a higher alcohol; or by reacting compound I with anhydrous HCl (obtained as a gas or from TMSCl or equivalent means) and dimethyl sulfite in a suitable solvent such as methanol; to form an ester compound of the formula (formula III)

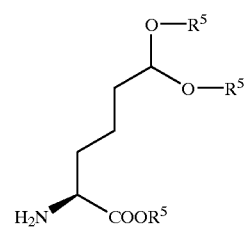

III wherein each $R^5$ is a $C_1-C_{18}$ alkyl (preferably $C_1-C_{10}$ alkyl, more preferably lower alkyl, and most preferably methyl) In the above esterification step conditions are not known to be critical, for example, a temperature of about 0 to about 45° C., preferably about 35 to about 40° C., for a reaction time of about 8 to about 72 hours (h), preferably about 6 to about 9 h, is typically adequate; it is preferred that the step takes place in an atmosphere such as HCl, nitrogen or argon. The reaction will result in either a full amino group or an amino salt, either of which can be used in the reaction described in Rob1.

To prepare the keto starting material for the enzymatic reductive amination process for the invention, a halo alkyl compound having the formula (formula IV) is used as a starting material wherein n is one to five (preferably 2) and X is Cl, Br or I (preferably Br). Preferably the bromo derivative of the formula IV is reacted with magnesium to form the organomagnesium derivative of the compound of formula IV which is subsequently reacted with an alpha dicarbonyl compound such as diethyl (preferred) or dimethyl oxalate at low temperature in tetrahydrofuran (THF) to afford an ester (methyl or ethyl) of the compound having formula II. The ester derivative of formula II is subsequently saponified as depicted in Scheme 1 to afford the derivative of formula II having $R^1$=H, or more preferably it is saponified as depicted in scheme 2 and isolated as the derivative for formula II having $R^1$=Li.

IV n = 1 to 5
X = Cl, Br or I

The halo derivatives having formula IV wherein n=2 or 3 can be prepared by reacting HBr with the appropriate starting compound (tetrahydrofuran or tetrahydropyran), followed by oxidation to an aldehyde using standard conditions and finally reacting the halo aldehyde with the appropriate alcohol (methyl, ethyl or propyl) or diol (ethylene glycol, 1,3-dihydroxy propane, 1,3-dihydroxy-2, 2-dimethyl propane) to afford a compound having formula IV. Alternatively compounds of formula II can be prepared starting from the appropriate commercially available halo alcohols, aldehydes or acetals using the chemistry depicted in Schemes 1 or 2.

Scheme 1

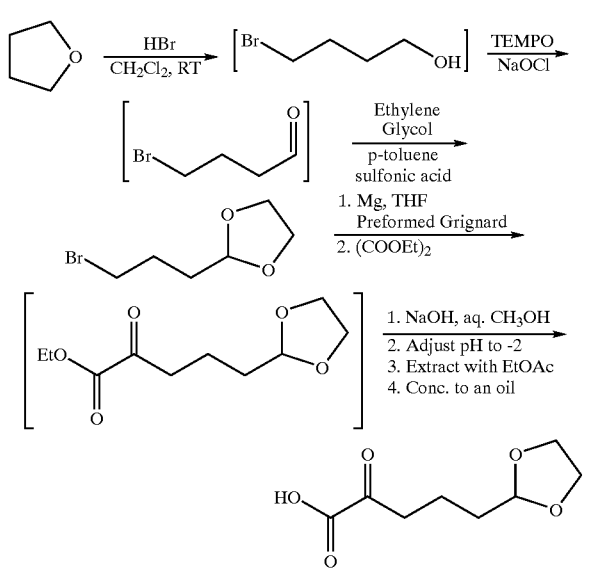

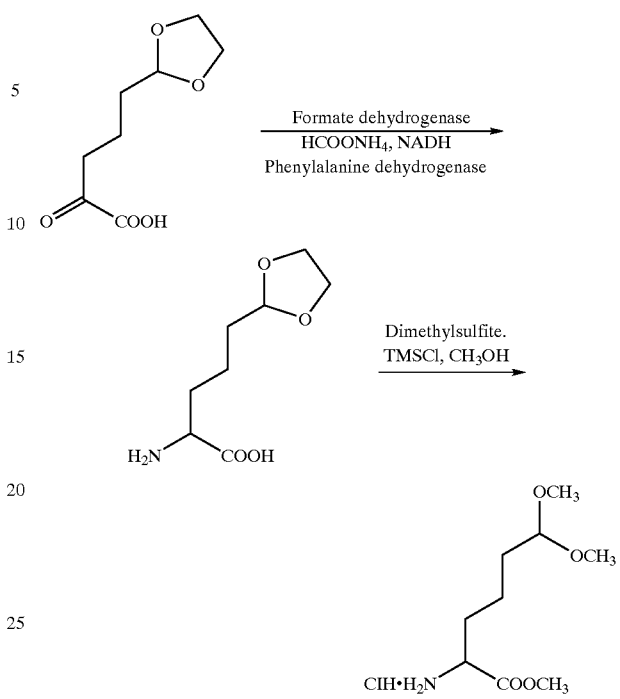

Another exemplary process of the invention is depicted below (Scheme 2).

Scheme 2

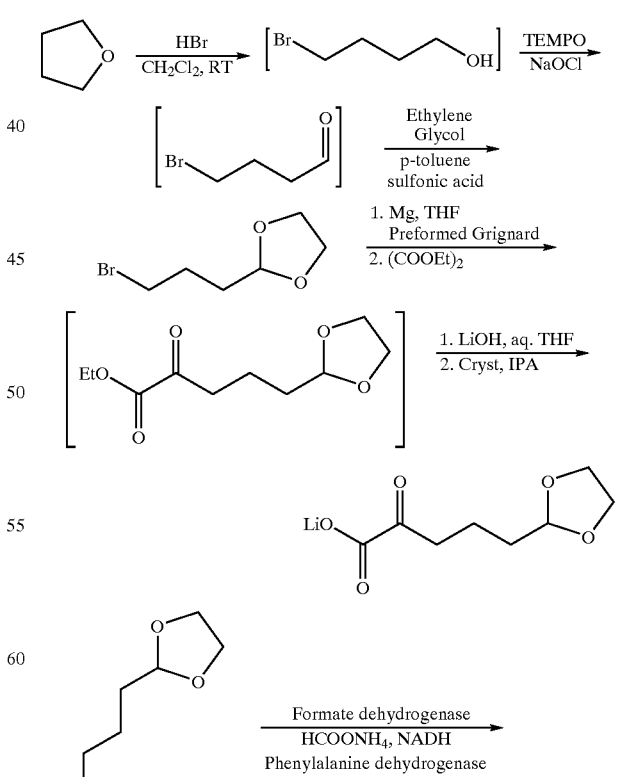

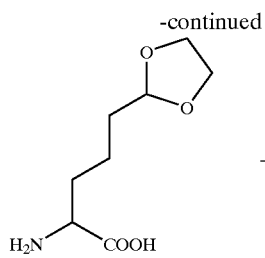

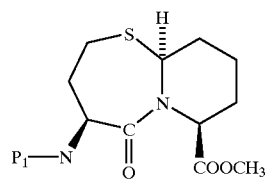

Dimethylsulfite.
TMSCl, CH₃OH
→

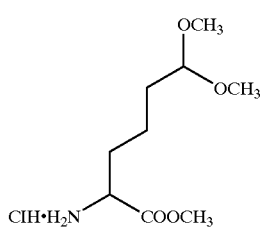

As described in Rob1 in U.S. Pat. No. 5,508,272, the compound produced by the present process (formula III herein, formula XXIII in Rob1) or its acid addition salt, for example, (S)-2-amino-6,6-dimethoxyhexanoic acid, methyl ester, can be coupled with the N-protected amino acid of the formula (formula V)

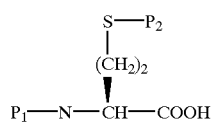

V to give the dipeptide of the formula (formula VI)

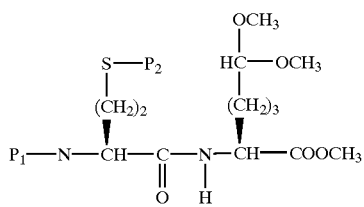

VI wherein $P_1$ is an amino protecting group such as benzyloxycarbonyl or t-butyloxycarbonyl or a group which together with the N-atom forms a protecting group such as phthalimido and $P_2$ is a mercapto protecting group such as acetyl or benzoyl. This coupling reaction is preferably performed in the presence of a coupling reagent such as benzotriazol-1-yloxytris(dimethylamino)phosphonium hexafluorophosphate, ethyl-3-(3-dimethyl-amino)propyl carbodiimide, dicyclohexylcarbodiimide, or 1H-benzotriazol-1-ol, methane sulfonate ester.

The $P_2$ protecting group is selectively removed from the dipeptide of formula VI such as by treatment with sodium methoxide in methanol or by treatment with p-toluenesulfonic acid in methanol. The resulting mercaptan compound is then subjected to an acid catalyzed cyclization reaction preferably by treating with a strong acid such as trifluoroacetic acid, p-toluenesulfonic acid, methanesulfonic acid, or a commercially available polystyrene sulfonate polymer type ion exchange resin such as Amberlyst15®. This cyclization reaction can be performed in a non-protic solvent such as methylene chloride or chloroform to give the lactam of the formula (formula VII)

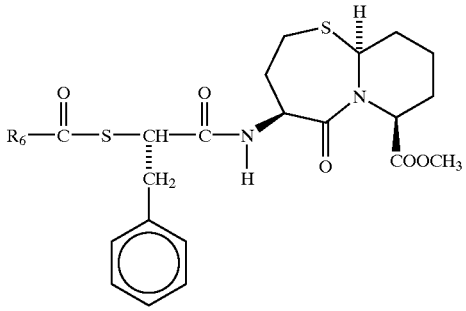

VII

The lactam of formula VII is then treated to remove the $P_1$ N-protecting group and then reacted with the acylmercaptoalkanoyl sidechain of the formula (formula VIII)

VIII $$R_6-\overset{O}{\overset{\|}{C}}-S-\overset{(S)}{\underset{\underset{\displaystyle \phi}{CH_2}}{CH}}-\overset{O}{\overset{\|}{C}}-OH$$

wherein $R_6$ is methyl or phenyl giving the compound of the formula (formula IX)

IX

This coupling reaction can be performed in an organic solvent such as methylene chloride and in the presence of a coupling reagent such as 1-ethyl-3-(3-dimethylaminopropyl)carbodiimide, dicyclohexylcarbodiimide, benzotriazol-1-yloxytris-(dimethylamino)phosphonium hexafluorophosphate, or carbonyldiimidazole. Alternatively, the acylmercaproalkanoic acid of formula VIII can be converted to an activated form prior to coupling such as an acid chloride, mixed anhydride, symmetrical anhydride, activated ester, etc.

The $P_1$ N-protecting group can be removed from the lactam of formula VII, for example, by treatment with hydrazine monohydrate when $P_1$ together with the N-atom forms a phthalimido group or by treatment with iodotrimethylsilane or palladium on carbon and hydrogen when $P_1$ is benzyloxycarbonyl or by treatment with hydrochloric acid in dioxane or other strong acid when $P_1$ is t-butoxycarbonyl.

The acyl group $R_4$—C(O)— is removed and the methyl ester group is converted to the carboxylic acid from the compound of formula IX to give the desired final product. For example, when R is methyl, treatment with methanolic sodium hydroxide followed by aqueous acid yield the desired compound.

4S-[4a(R*),7a, 10ab]]-Octahydro-4-[(2-mercapto-1-oxo-3-phenylpropyl)amino]-5-oxo-7H-pyrido[2,1-b][1,3]thiazepine-7-carboxylic acid possesses angiotensin converting enzyme and neutral endopeptidase inhibitory activity. This compound as well as its pharmaceutically acceptable salts are useful in treating cardiovascular diseases such as hypertension and congestive heart failure as noted in Robl U.S. Pat. No. 5,508,272. This compound can be administered to a mammalian host such as man at from about 0.1 mg to about 100 mg per kg of body weight per day, preferably from about 0.5 mg to about 25 mg per kg of body weight per day. The compound is preferably administered orally but parenteral routes and topical routes can also be employed. The daily dose can be administered singly or can be divided into two to four doses administered throughout the day.

The present invention also concerns an engineered yeast host cell comprising a recombinant or endogenous nucleic acid sequence coding for formate dehydrogenase (FDH) and a recombinant nucleic acid sequence coding for a phenylalanine dehydrogenase (PDH). Preferably, the nucleic acid molecules are DNA molecules and the nucleic acid sequences are DNA sequences. All DNA sequences are represented herein by formulas whose left to right orientation is in the conventional direction of 5' to 3'. It is also contemplated that the present invention encompasses modified sequences. As used in the present application, the term "modified", when referring to a nucleotide or polypeptide sequence, means a nucleotide or polypeptide sequence which differs from the wild-type sequence found in nature.

The recombinant host cell of the present invention can be any microorganism that is cabable of producing recombinant and/or native (endogenous) FDH and is capable of being transformed or genetically engineered with PDH from a different species to express catalytically active PDH. Examples of host cells of the invention include, for example, Candida species, Saccharomyces species, Cephalosporium species, Fusarium species, Penicillium species, *Pichia pastoris*, Candida species, Escherichia species and Pseudomonas species. The most preferred host cell of the invention is a Pichia species, particularly *Pichia pastoris*.

The PDH nucleic acid used to transform the yeast host cell can be any nucleic acid capable of resulting in expression of catalytically active PDH in the host cell. For example, the PDH nucleic acid sequence coding for PDH source can be *Bacillus sphaericus, Bacillus badius, Sporosarcina ureae, Bacillus faecalis, Corynebacterium equis, Rhodotorula glutinis,* Brevibacterium sp., Rhodococcus sp. such as *Rhodococcus maris,* and the like. Preferred PDH nucleic acid is the PDH gene from *Thermoactinomyces intermedius* ATCC 33205, as disclosed by Takada, H., et al.,*J. Biochem.,* 109, 371–376 (1991), the disclosure of which is incorporated herein by reference in its entirety.

The PDH (and, optionally FDH) sequence of the present invention used to transform the yeast host cell can be obtained using various methods well-known to those of ordinary skill in the art. At least three alternative principal methods may be employed:

(1) the isolation of a double-stranded DNA sequence from genomic DNA or complementary DNA (cDNA) which contains the sequence;

(2) the chemical synthesis of the DNA sequence; and (3) the synthesis of the DNA sequence by polymerase chain reaction (PCR).

In the first approach, a genomic or cDNA library can be screened in order to identify a DNA sequence coding for all or part of PDH (and, optionally FDH). For example, a *T. intermedius* genomic DNA library can be screened in order to identify the DNA sequence coding for all or part of PDH (and, optionally FDH). Various techniques can be used to screen the genomic DNA or cDNA libraries.

For example, labeled single stranded DNA probe sequences duplicating a sequence present in the target genomic DNA or cDNA coding for all or part of PDH can be employed in DNA/DNA hybridization procedures carried out on cloned copies of the genomic DNA or cDNA which have been denatured to single stranded form.

A genomic DNA or cDNA library can also be screened for a genomic DNA or cDNA coding for all or part of PDH (and, optionally FDH) using immunoblotting techniques.

In one typical screening method suitable for either immunoblotting or hybridization techniques, the genomic DNA library, which is usually contained in a vector, or cDNA library is first spread out on agar plates, and then the clones are transferred to filter membranes, for example, nitrocellulose membranes. A DNA probe can then be hybridized or an antibody can then be bound to the clones to identify those clones containing the genomic DNA or cDNA coding for all or part of PDH (and, optionally FDH).

In the second approach, the DNA sequences of the present invention coding for PDH (and, optionally FDH) can be chemically synthesized. For example, the DNA sequence coding for PDH (and, optionally FDH) can be synthesized as a series of 100 base oligonucleotides that can be sequentially ligated (via appropriate terminal restriction sites or complementary terminal sequences) so as to form the correct linear sequence of nucleotides.

In the third approach, the DNA sequences of the present invention coding for PDH (and, optionally FDH) can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, White et al., Trends Genet, 5,185–189 (1989).

The DNA sequences useful in the present invention coding for PDH (and, optionally FDH) can also be modified (i.e., mutated) to prepare various mutations. Such mutations may be either degenerate, i.e., the mutation changes the amino acid sequence encoded by the mutated codon, or non-degenerate, i.e., the mutations does not change the amino acid sequence encoded by the mutated codon. These modified DNA sequences may be prepared, for example, by mutating the PDH (and, optionally FDH) DNA sequence so that the mutation results in the deletion, substitution, insertion, inversion or addition of one or more amino acids in the encoded polypeptide using various methods known in the art. For example, the methods of site-directed mutagenesis described in Morinaga et al., Bio/Technol. 2, 636–639 (1984), Taylor et al., Nucl. Acids Res. 13, 8749–8764 (1985) and Kunkel, Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers et al., Nucl. Acids Res. 16, 791–802 (1988) may also be employed. Both degenerate and non-degenerate mutations may be advantageous in producing or using the polypeptides of the present invention. For example, these mutations may permit higher levels of production, easier purification, or provide additional restriction endonuclease recognition sites. All such modified DNA and polypeptide molecules are included within the scope of the invention.

The yeast cells of the invention can be conveniently transformed by use of expression vectors comprising a DNA sequence coding for PDH (and, optionally FDH). The expression vectors preferably contain all or part of one of the DNA sequences having the PDH nucleotide sequence substantially as shown in Takada, H., et al, *J. Biochem.*, 109, 371–376 (1991). Further preferred are expression vectors comprising one or more regulatory DNA sequences operatively linked to the DNA sequence coding for all or part of PDH (and, optionally FDH). As used in this context, the term "operatively linked" means that the regulatory DNA sequences are capable of directing the replication and/or the expression of the DNA sequence coding for PDH (and, optionally FDH)

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front (i.e., upstream of) the DNA sequence (preferably an inducible promoter such as AOX 1 or constitutive promoter such as GAP) and followed by the DNA sequence coding for all or part of PDH (and, optionally FDH). The DNA sequence coding for all or part of PDH (and, optionally FDH) is followed by transcription termination sequences and the remaining vector. If recombinant FDH nucleic acid is used, the FDH DNA can be part of the same vector as the PDH or may be part of a separate vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marker sequences which are capable of providing phenotypic selection in transformed host cells, stability elements such as centromeres which provide mitotic stability to the plasmid, and sequences which provide sites for cleavage by restriction endonucleases. The characteristics of the actual expression-vector used must be compatible with the host cell which is to be employed. For example, when cloning in a fungal or yeast cell system, the expression vector should contains promoters isolated from the genome of fungal or yeast cells (e.g., the trpC promoter from *Aspergillus nidulans*, the AOX1 promoter from *Pichia pastoris*, and the GAP promoter from *P. pastoris*). Certain expression vectors may contain an autonomously replicating sequence (ARS; e.g., ARS from *Fusarium oxysporium, Saccharomyces cerevisiae*, and the like) which promotes in vivo production of self-replicating plasmids in fungal or yeast hosts. It is preferred that the yeast expression vectors of the invention do not have a yeast ARS sequence and thus will integrate into host chromosomes upon plasmid entry of host cells. Such integration is preferred because of enhanced genetic stability. An expression vector as contemplated by the present invention is at least capable of directing the replication in and integration in yeast or fungal cells, and preferably the expression, of the PDH DNA sequence disclosed in Takada, H., et al. *J. Biochem.*, 109, 371–376 (1991) in Pichia cells. Suitable promoters include, for example, the trpC promoter from *Aspergillus nidulans*, the penicillin V amidase promoter from *P. pastoris*. Suitable termination sequences include, for example, the trpC terminator from *A. nidulans*, the PVA terminator for *F. oxysporum*, and the AOX1 transcription termination sequence of *P. pastoris*. It is also preferred that the expression vector include a sequence coding for a selectable marker. The selectable marker is preferably antibiotic resistance. As selectable markers, G418 resistance or Zeocin resistance can be conveniently employed. All of these materials are known in the art and are commercially available.

Particularly preferred are the expression vectors designated pPDH9k/10, pPDH155K, and pGAPk-PDH described herein below, which contain the DNA sequence coding for PDH, or expression vectors with the identifying characteristics of these plasmids. Also preferred is the expression vector designated pGAPZ-FDH containing a DNA sequence encoding FDH.

Host cell *Pischia pastoris* strain SMD1168 containing plasmid pPDH9K/10 was deposited with the American Type Culture Collection ("ATCC"), Manassas, Va., on Mar. 26, 1997 under the Budapest Treaty and is assigned ATCC accession no. 74408.

Host cell *Pichia pastoris* strain GS115 containing plasmids pGAPk-PDH and pGAPZ-FDH was deposited with the ATCC on Feb. 13, 1998 under the provisions of the Budapest Treaty and is assigned ATCC Accession No. 74433.

Host cell *Escherichia coli* strain BL21 containing plasmid pPDH155K was deposited with the ATCC on Mar. 26, 1997 under the provisions of the Budapest Treaty and is assigned ATCC Accession No. 98374.

Suitable expression vectors containing the desired coding and control sequences may be constructed using standard recombinant DNA techniques known in the art, many of which are described in Sambrook et al. Molecular Cloning: A Laboratory Manual, 2nd edition, Cold Spring Harbor Laboratory, Cold Spring Harbor, N.Y. (1989).

The host cells of the invention preferably contain an expression vector comprising one or more regulatory DNA sequences capable of directing the replication and/or the expression of and operatively linked to a DNA sequence coding for all or part of PDH. The host cells can be, for example, *Cephalosporium acremonium, Fusarium oxysporium* and *Penicillium chrysogenum, Pichia pastoris, Candida boidinii,* and *Saccharomyces cerevisiae* cells. Particularly preferred as host cells are *Pichia pastoris* strains.

Expression vectors may be introduced into host cells by various methods known in the art. For example, transformation of host cells with expression vectors can be carried out by the polyethylene glycol mediated protoplast transformation method. However, other methods for introducing expression vectors into host cells, for example, electroporation, biolistic injection, or protoplast fusion, can also be employed.

Once an expression vector has been introduced into an appropriate host cell, the host cell may be cultured under conditions permitting expression of large amounts of the desired polypeptide, in the preferred case a polypeptide molecule comprising PDH (and, optionally, FDH). Thus, the present invention concerns an engineered host cell, preferably yeast, capable of producing both phenylalanine dehydrogenase (PDH) and formate dehydrogenase (FDH) wherein said host cell comprises (a) recombinant nucleic acid encoding PDH and, optionally, endogenous nucleic acid encoding PDH, and (b) nucleic acid encoding FDH wherein said nucleic acid is endogenous, recombinant or both endogenous and recombinant.

Host cells containing an expression vector which contains a DNA sequence coding for all or part of PDH (and, optionally, FDH) may be identified by one or more of the following five general approaches: (a) DNA—DNA hybridization; (b) the presence or absence of marker gene functions; (c) assessing the level of transcription as measured by the production of mRNA transcripts in the host cell; (d) detection of the gene product immunologically; and (e) enzyme assay, enzyme assay being the preferred method of identification.

In the first approach, the presence of a DNA sequence coding for all or part of the desired enzyme can be detected by DNA—DNA or RNA–RNA hybridization using probes complementary to the DNA sequence.

In the second approach, the recombinant expression vector host system can be identified and selected based upon the presence or absence of certain marker gene functions (e.g., acetamide utilization, resistance to antibiotics, resistance to fungicide, uracil prototrophy, etc.). A marker gene can be placed in the same plasmid as the DNA sequence coding for all or part of the enzyme under the regulation of the same or a different promoter used to regulate the enzyme coding sequence. Expression of the marker gene in response to induction or selection indicates the presence of the entire recombinant expression vector which carries the DNA sequence coding for all or part of the desired enzyme.

In the third approach, the production of enzyme mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of the desired enzyme can be assessed immunologically, for example, by Western blotting.

In the fifth approach, expression of the enzyme can be measured by assaying for enzyme activity using known methods.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977).

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

If a host cell is used which is engineered to express recombinant FDH, then procedures similar to those described above can be used and adapted to transform host cells to contain nucleic acid encoding FDH. A suitable source of FDH nucleic acid is Pichia species.

It is preferred that the PDH transformed host cells of the invention also contain native or endogenous nucleic acids which are capable of expressing FDH. Optionally, the host cells can also contain endogenous nucleic acid encoding PDH in addition to recombinant PDH nucleic acid. Thus, the host cell chosen in which to insert an expression vector preferably already has the ability to express FDH. It has been unexpectedly discovered that transformation of Pichia cells with a vector capable of directing expression of PDH also resulted in enhanced expression of FDH. Use of such cells in the enzymatic conversion process of the invention is preferred.

The present invention further concerns a method for producing PDH and FDH comprising culturing an engineered host cell containing recombinant or native nucleic acid capable of expressing FDH and containing an expression vector capable of expressing PDH. Preferably the expression vector is pPDH9K/10.

All amino acid residues identified herein are in the natural L-configuration. In keeping with standard polypeptide nomenclature, J. Biol. Chem. 243, 3557–3559 (1969), abbreviations for amino acid residues are as shown in the following Table of Correspondence.

| TABLE OF CORRESPONDENCE | | |
|---|---|---|
| SYMBOL 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-aspargine |
| C | Cys | L-cysteine |

All amino acid sequences are represented herein by formulas whose left to right orientation is in the conventional direction of amino-terminus to carboxy-terminus.

It will be understood that allelic variations of the nucleic acid and amino acid sequences useful herein naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphatic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

The following examples illustrate the invention but should not be interpreted as a limitation thereon. The reaction in examples 1–6 is shown in scheme 3.

Scheme 3

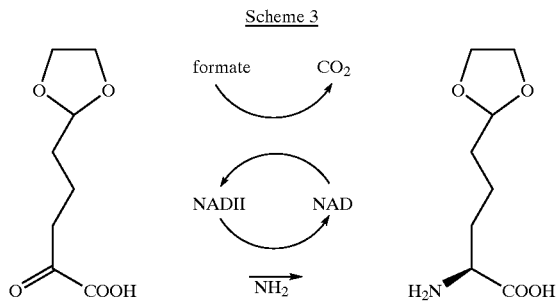

EXAMPLE 1

Reductive Amination With Amino Acid Dehydrogenases From Various Sources

Solutions contained in a final volume of 1.0 ml at pH 8.7: 1 M ammonium formate (adjusted to pH 8.7 with $NH_4OH$). 0.1 M 5-(1,3-dioxolan-2-yl)-2-oxo-pentanoic acid, 1 mM NAD, 1 milligram (mg) protein/milliliter (ml) (0.53 units/mg protein from Boehringer Mannheim) formate dehydrogenase from *Candida boidinii*, and the amino acid dehydrogenases listed in table 1. The solutions were incubated at 30° C. for 16 h, then samples were taken from the reactions for high performance liquid chromatography (HPLC) analysis. The results are shown in Table 1. Enantiomeric excess was greater than 98% in each case.

TABLE 1

| Dehydrogenase | Source | Amount Units | 5-(1.3-dioxolan-2-yl-(S)-2-aminopentanoic acid mM |
| --- | --- | --- | --- |
| Glutamate | Sigma | 76 | 1.03 |
| Alanine | Sigma | 35.7 | 11.77 |
| Leucine | in-house | 22 | 14.01 |
| Phenylalanine | Sigma | 12.6 | 51.71 |

Leucine dehydrogenase was partially purified from *Bacillus sphaericus* ATCC 4525. Glutamate dehydrogenase was from beef liver; alanine dehydrogenase was from *Bacillus subtilis*; phenylalanine dehydrogenase was from Sporosarcina species.

HPLC Assay of 5-(1,3-dioxolan-2-yl)-(S)-2-aminopentanoic acid Optical Purity and Amount Samples were diluted with water to about 5 mM concentration and placed in a boiling water bath for 1 minute to stop reactions and precipitate proteins. After cooling, the samples were filtered through 0.2 micron nylon filters into HPLC vials.
  column: Chiralpak WH 25×0.46 cm (Daicel Chemical Industries, Ltd.)
  mobile phase: 0.3 mM $CuSO_4$
  flow rate: 1 ml/minute (min)
  column temperature: 40° C.
  detection: DAD set at 230 nanometer (nm)
  injection volume: 20 microliter ($\mu$l)
Retention times: L-enantiomer 28.044 min, D-enantiomer 23.842 min. Retention times decrease with use of column and can change with concentration of samples. The minimum percentage of D-enantiomer that can be detected is about 1%.

EXAMPLE 2

Reductive Amination With Extract From *Thermoactinomyces intermedius*

*Thermoactinomyces intermedius* ATCC33205 was grown in a 15 L fermentor at 55° C. on medium containing 1.0% L-phenylalanine, 0.1% L-glutamic acid, 1.0% peptone, 0.5% yeast extract, 0.2% $K_2HPO_4$, 0.1% NaCl and 0.02% $MgSO_4.7H_2O$. Cells were harvested 19 h after inoculation and stored frozen at −12° C. Frozen cell paste (8.0 g) was washed with 200 ml 50 mM potassium phosphate buffer pH 7 and centrifuged at 16000×g for 10 min. The cells were resuspended in 40 ml of 50 mM potassium phosphate buffer pH 7 containing 1 mM dithiothreitol. The cell suspension was sonicated for 2 min, then centrifuged at 16000×g for 10 min. The supernatant contained 0.43 units PDH/mg protein when assayed for reductive amination of phenylpyruvate.

A 400 ml pH 8.7 solution was prepared containing 1 M ammonium formate (25.22 g), 0.1 M 5-(1,3-dioxolan-2-yl)-2-oxo-pentanoic acid (7.527 g), 1 mM NAD (274 mg), 1 mM dithiothreitol (61.6 mg) 40 u (76 mg protein) formate dehydrogenase, and 40 ml (309 mg protein) of the *Thermoactinomyces intermedius* extract. The ammonium formate was dissolved in 300 ml water, brought to pH 8.7 with concentrated ammonium hydroxide, then the other components were added and the solution was brought to 400 ml and again adjusted to pH 8.7 with concentrated ammonium hydroxide. The solution was incubated at 40° C. Additional 20 mg portions of formate dehydrogenase were added at 9 h and 23 h. After 21 h, the solution contained 80.1 mM L-5-(1,3-dioxolan-2-yl)-(S)-2-amino-pentanoic acid as measured by HPLC analysis. The concentration remained the same after 29 h. The enantiomeric excess as measured by chiral HPLC was greater than 98%.

EXAMPLE 3

Reductive Amination With Heat-dried *Thermoactinomyces intermedius* and Heat-dried *Candida boidinii*

5-(1,3-dioxolan-2-yl)-2-oxo-pentanoic acid (10.0 g, 53.14 mmoles), ammonium formate (3.509 g, 55.65 mmoles), and a magnetic stirring bar were added to a 300 ml beaker. 150 ml water and a 4.5 ml concentrated ammonium hydroxide solution (29.6%) were added to the beaker and stirred until the solids were dissolved. The pH was adjusted to 8 by adding additional ammonium hydroxide as necessary. Dithiothreitol (36.2 mg, 0.235 mmoles) and NAD (145.2 mg, 0.212 mmoles) were added and stirred to dissolve. Water was added to bring the volume to 200 ml and the solution was poured into a 250 ml jacketed reactor. The beaker was rinsed with 6 ml water and the rinse was added to the reactor. The reactor was maintained at 40° C. with a Neslab RTE-110 bath/circulator. The solution was stirred at 280 revolutions per minute (RPM) with a Heidolph RZR-2000 stirrer. *Thermoactinomyces intermedius* heat-dried cells (4.08 g, 333 u phenylalanine dehydrogenase) and *Candida boidinii* heat-dried cells (1.42 g, 55 u formate dehydrogenase) were added to the stirred solution. After 30 min the cells were dispersed by the stirrer. At this time the pH was brought from about 7.1 back to pH 8 by addition of concentrated ammonium hydroxide solution (about 0.5 ml).

The reactor was kept covered with parafilm to minimize evaporation. After 3 h, a small addition of ammonium hydroxide was required to adjust the pH to 8.0. Thereafter the pH rose to 8.1 to 8.2 after 6 h, and about 8.5 after 19 h. After the conversion of 5-(1,-dioxalan-2-yl)-2-oxo-pentanoic acid to 5-(1,3-dioxalan-2-yl)-(S)-2-amino-pentanoic acid was complete, as judged by HPLC, cells were removed by centrifugation of the suspension for 15 min at 13,000 rpm in the Sorvall GSA rotor (27.504×g). The cell pellet was resuspended using a glass rod in 20 ml water and centrifuged for 10 min at 20,000 rpm (47.807×g) in the Sorvall SS34 rotor. This wash step was repeated 3 more times, and the supernatants were combined with the first supernatant. The HPLC yield at the end of the reaction was 6.85 g 5-(1,3-dioxolan-2-yl)-(S)-2-amino-pentanoic acid (74.9 M % corrected for the 91% HPLC purity of the input ketoacid). The enantiomeric excess was greater than 98%.

EXAMPLE 4

Reductive Amination With Heat-dried Recombinant *E. coli* and Heat-dried *Candida boidinii*

5-(1,3-dioxalan-2-yl)-2-oxo-pentanoic acid (20.0 g, 106.28 mmoles), ammonium formate (7.018 g, 111.29 mmoles), and a magnetic stirring bar were added to a 500 ml beaker, 300 ml water and 9 ml concentrated ammonium hydroxide solution (29.6%) were added to the beaker and stirred until the solids were dissolved. The pH was adjusted to 8 by adding additional ammonium hydroxide as necessary. Dithiothreitol (65.6 mg, 0.425 mmoles) and NAD (282 mg, 0.425 mmoles were added and stirred to dissolve. Water was added to bring the volume to 400 ml and the solution was poured into a 1-liter (L) jacketed reactor. The beaker was rinsed with 12 ml water and the rinse was added to the reactor. The reactor was maintained at 40° C. with a Neslab RTE-110 bath/circulator. The solution was stirred at 350 RPM with a Heidolph RZR-2000 stirrer. *E. coli* BL21 (DE3) (pPDH155K) [SC16144] heat-dried cells (0.360 g, 666 u phenylalanine dehydrogenase) and *Candida boidinii* heat-dried cells (3.116 g, 110 u formate dehydrogenase) were added to the stirred solution. After 5 to 10 min the cells were dispersed by the stirrer. At this time the pH was brought from about 7.2 back to pH 8 by addition of concentrated ammonium hydroxide solution (about 1.4 ml). The reactor was kept covered with parafilm to minimize evaporation. After 3 h, a small addition of ammonium hydroxide was required to adjust the pH to 8.0. Thereafter the pH rose to about 8.4 after 16 h. When the conversion of 5-(1,3-dioxalan-2-yl)-2-oxo-pentanoic acid to 5-(1,3-dioxolan-2-yl)-(S)-2-amino-pentanoic acid was complete, as measured by HPLC, the suspension was removed from the reactor and stored at 4° C. until removal of cells. Cells were removed by filtration on a Buchner funnel with the acid of a celite admix and precoat. The filtrate was then ultrafiltered with a 10,000 molecular weight (MW) cutoff polysulfone membrane. The HPLC yield at the end of the reaction and filtrations was 12.5 g 5-(1,3-dioxolan-2-yl)-(S)-2-amino-pentanoic acid (71.0 M % corrected for the 88% HPLC purity of the input ketoacid).

EXAMPLE 5

Reductive Amination With Recombinant Pichia

An extract of *Pichia pastoris* strain SMD1168 containing plasmid pPDH9K/10 (ATCC accession no. 74408) was prepared by suspending 100 mg cells per ml in 50 mM potassium phosphate buffer pH 7.3 containing 1 mM dithio-threitol and 0.2% Triton X-100 and disrupting for 5 min at 4° with a bead mill containing glass beads. The extract was microfuged for 5 min at 10000 rpm. The extract contained 2.44 units (u)/ml formate dehydrogenase and 15.4 u/ml phenylalanine dehydrogenase and the activity of the wet cells was taken as 24.4 u/g wet cells formate dehydrogenase and 154 u/g wet cells phenylalanine dehydrogenase. 5-(1, 3-dioxalan-2-yl)-2-oxo-pentanoic acid (Li salt) (1.0 g, 5.1517 mmoles) and ammonium formate (389.8 mg, 6.182 mmoles) were dissolved in 20 ml water. Dithiothreitol (3.28 mg, 0.0213 mmoles) and NAD (14.1 mg, 0.0206 mmoles) were added. The pH of the solution was 8.16.

a. Pichia extract (0.112 ml containing 0.273 u formate dehydrogenase and 1.723 u phenylalanine dehydrogenase) was added to 1 ml of the solution containing the ketoacid and incubated for 25 h in a capped microfuge tube at 40° C. The HPLC yield at the end of the reaction was 0.038 g 5-(1,3-dioxolan-2-yl)-(S)-2-amino-pentanoic acid (92.6 M % corrected for 93% HPLC purity and 9.4% Karl Fischer (KF) water of the input ketoacid. Enantiomeric excess was greater than 98%.

b. The remaining 19 ml of solution containing the substrate was added to Pichia wet cells (0.214 g containing 5.23 u formate dehydrogenase and 32.93 units phenylalanine dehydrogenase) in a 50 ml Erlenmeyer flask. The pH of the suspension was 8.04. The cells had been stored frozen at −15° C. The flask was capped with parafilm and incubated on a rotary shaker at 40° C. and 200 rpm for 25 h. The HPLC yield at the end of the reaction was 0.7506 g 5-(1,3-dioxolan-2-yl)-(S)-2-amino-pentanoic acid (96.2 M % corrected for 93% HPLC purity and 9.4% KF water of the input ketoacid. Enantiomeric excess was greater than 98%.

c. Deionized water (200 ml), ammonium formate (7.796 g, 123.63 mmoles), and 5-(1,3-dioxolan-2-yl)-2-oxo-pentanoic acid, lithium salt (20 g, 103.03 mmoles) were added to a 500-ml jacketed reactor maintained at 40° C. and stirred at 250 RPM. After the solids had dissolved, NAD (66.34 mg, 0.1 mmoles), and heat-dried Pichia (1.6406 g containing 666 units phenylalanine dehydrogenase and 150 units formate dehydrogenase) were added. The pH was adjusted to 8.0 with conc. $NH_4OH$. The pH was adjusted from 8.76 to 8 by addition of formic acid (99%) after 7 h. The pH was again adjusted to 8 with formic acid after 10 and 23 h. After 25 h the yield of 5-(1,3-dioxolan-2-yl)-(S)-2-amino-pentanoic acid was 17.16 g ((98.3%) corrected for purity of the input ketoacid. Enantiomeric excess was greater than 98%. Cells were removed by centrifugation and protein was removed by ultrafiltration.

EXAMPLE 6

Reductive Amination With Immobilized Enzymes

Phenylalanine dehydrogenase from a recombinant *E. coli* extract was immobilized on Eupergit C250L (from Rohm GmbH) and formate dehydrogenase from *Candida boidinii* extract was immobilized on Eupergit C (from Rohm GmbH) according to the directions of the manufacturer. The reactions contained in a volume of 100 ml: 5-(1,3-dioxolan-2-yl)-2-oxo-pentanoic acid, lithium salt (5.0 g, 25.8 mmoles), ammonium formate (1.754 g, 27.8 mmoles), dithiothreitol (16.4 mg, 0.106 mmoles), NAD (70.5 mg, 0.103 mmoles), recombinant phenylalanine dehydrogenase immobilized on Eupergit C250L (4.35 g, 166.5 units), and *Candida boidinii* formate dehydrogenase immobilized on Eupergit C (7.29 g, 27.5 units). pH was adjusted to 8.0 with NH$_4$OH and formic acid, and temperature was 40° C. At the end of each reaction, the solution was drained from the reactor through a stainless steel sieve, 80/400 mesh, which retained the immobilized enzymes, then fresh solution was added to the reactor. The enzymes were used for 6 reactions as shown in the table. Enantiomeric excess was greater than 98% for each reaction.

| Use | Reaction Time H | 5-(1,3-dioxolan-2-yl)-(S)-2-amino pentanoic acid g | Yield corrected for purity of input % |
|---|---|---|---|
| 1 | 26 | 2.76 | 61.9 |
| 2 | 26 | 2.70 | 60.5 |
| 3 | 45 | 3.73 | 83.5 |
| 4 | 69 | 4.37 | 97.8 |
| 5 | 48 | 3.03 | 67.9 |
| 6 | 120 | 3.83 | 85.8 |

EXAMPLE 7

Pichia Recombinant for *C. boidinii* Formate Dehydrogenase and *T. intermedius* Phenylalanine Dehydrogenase Deionized water (10.0 ml), ammonium formate (389.8 mg, 6.18 mmoles), and 5-(1,3-dioxolan-2-yl-2-oxo-pentanoic acid, lithium salt (1.0 g, 5.15 mmoles) were added to a 50-ml Erlenmeyer flask and mixed on a rotary shaker at 40° C. and 200 rpm. After the solids had dissolved, NAD (3.32 mg, 0.005 mmoles), and wet cells of Pichia strain SC16245 double constitutive recombinant for *T. intermedius* phenylalanine dehydrogenase and *C. boidinii* formate dehydrogenase (0.67 g containing 40.9 units phenylalanine dehydrogenase and 7.24 units formate dehydrogenase) were added. The pH was adjusted to 8.0 with conc. NH$_4$OH. The flask was capped with parafilm and incubated on a rotary shaker at 40° C. and 200 rpm. After 25 h the yield of 5-(1,3-dioxolan-2-yl)-(S)-2-amino-pentanoic acid was 0.98 g (100%) corrected for purity of the input ketoacid. The enantiomeric excess was greater than 98%.

EXAMPLE 8

The following process description details the procedure used to prepare 91.5 g (77.9 M %) of 4-(3-bromopropyl)-1,3-dioxolane from THF.

Preparation of 4-(3-bromopropyl)-1,3-dioxolane

THF (50 mL) and dichloromethane (500 mL) were added to a 1 L three neck flask equipped with a nitrogen inlet, a thermocouple, an HBr sparge tube and a gas vent. HBr gas (~63 g) was charged to the solution while maintaining the reaction temperature between 20 and 25° C. The addition of HBr gas was continued until the reaction was judged complete (GC Area % for THF is <10%, actual 3.5 Area %).

Subsequently, the reaction mixture was purged with nitrogen to remove excess HBr gas and washed with 8 w/v % sodium bicarbonate (2×220 mL) to afford a methylene chloride solution of 4-bromo-butanol (GC Area %=90.5, apparent pH=6.9). The resulting solution of 4-bromo-butanol and potassium bromide solution (5 g in 25 mL) was added to a 2 L three necked round bottomed flask equipped with an overhead stirrer, nitrogen inlet, thermocouple and a 1 L pressure equalizing addition funnel. With agitation, the contents of the reaction flask were cooled to −5 to +5° C. To the reaction flask, an 8 w/v % sodium bicarbonate solution (81 mL) and 2,2,6,6-tetramethyl-1-piperidinyloxy, free radical (0.675 g) were added. With vigorous stirring, titrated 5.25% sodium hypochlorite solution (874 mL) was added to the reaction mixture over ~1 hour maintaining the temperature in the range −5 to +25° C. Following complete addition the reaction was complete as judged by in-process GC analysis (<3 Rel A % 4-bromobutanol). The phases were allowed to separate and the aqueous layer was extracted with methylene chloride (150 mL). The combined organic layers were washed with aqueous acidified potassium iodide solution (1.19 g of potassium iodide in 125 mL of 10 w/v % HCl), 6.4 w/v % sodium thiosulfate solution (125 mL) and water (2×125 mL). The resulting methylene chloride solution of 4-bromobutanal (GC AP=91.5), ethylene glycol (39.0 g) and para-toluenesulfonic acid (7.25 g) were charged to a 2 L three neck round bottomed flask equipped with an overhead stirrer, nitrogen inlet, thermocouple heater and a Dean-Stark water separator with condenser. The reaction mixture was heated to reflux with azeotropic removal of water, until the reaction was complete as judged by GC analysis (<2 area % 4-bromobutanal unreacted). After cooling to 20 to 25° C., the reaction mixture was washed with 10 w/v % potassium carbonate solution (250 mL) and water (2×250 mL). The resulting methylene chloride solution of 4-(3-bromopropyl)-1,3-dioxolane was concentrated to one-half the original volume and tetrahydrofuran was added. Concentration was continued until less than 0.2% methylene chloride was present in the product solution containing 91.5 g of 4-(3-bromopropyl)-1,3-dioxolane (77.9 M %, GC area %=89.4, retention time of 7.9 min).

In-Process GC method:

Instrument: HP 5890 Series II Gas Chromatograph

Injector Temp: 200° C.

Column: Restek RTx-5; 30 m; 0.32 mm ID

Oven Program: 2 min@50° C., ramp up at 25° C./min to 275° C., 8 min@275° C.,

Detection: FID

Detector temperature: 300° C.

Sample preparation: dilute with methylene chloride

| Retention times | |
|---|---|
| 4-bromobutanol | 6.4 min |
| 4-bromobutyraldehyde | 5.6 min |
| 4-(3-bromopropyl)-1,3-dioxolane | 7.9 min |
| Late eluting impurity in BMS-207170 | 10.8 min |

(4-(3-bromopropyl)-1,3-dioxolane)-$^1$H-NMR: 300 MHz; CDCl$_3$: δ1.8 (m, 2H), 2.0 (m, 2H), 3.45 (tr, 2H), 3.85 (m, 24), 3.95 (m, 2H) and 4.9 (tr, 1H). $^{13}$C-NMR: 75 MHz; CDCl$_3$: δ26.94, 32.03, 33.46, 64.72 and 103.42.

EXAMPLE 9

The following process description details the procedure used to prepare 34 g (68 M %) of Lithium-5-(1,3-dioxolan-2-yl)-2-oxo-pentanoate from 50 g of 4-(3-bromopropyl)-1,3-dioxolane.

Preparation of Lithium-5-(1,3-dioxolan-2-yl)-2-oxo-pentanoate

Under a nitrogen atmosphere, magnesium (6.55 g) and dry tetrahydrofuran (30 mL) were charged to a clean dry 500 mL three neck flask. To this suspension, a tetrahydrofuran solution of 4-(3-magnesiobromopropyl)-1,3-dioxolane (5 mL) was added and the mixture was stirred for 10 to 30 minutes. A tetrahydrofuran solution of 4-(3-bromopropyl)-1,3-dioxolane was prepared by dissolving the bromoacetal (50 g) in tetrahydrofuran (130 mL). Following observation of an exotherm (2–7° C.), a tetrahydrofuran solution of 4-(3-bromopropyl)-1,3-dioxolane (5 mL) was added to the reaction mixture. Following observation of an exotherm (2–5° C.), the remaining tetrahydrofuran solution of 4-(3-bromopropyl)-1,3-dioxolane was added to the reaction mixture slowly over 2 to 4 hours maintaining the temperature in the range of 25 to 35° C. Following complete addition, the reaction mixture was stirred until formation of the grignard reagent was complete as judged by in-process GC assay (<1% unreacted bromide). Diethyl oxalate (29.85 g) and tetrahydrofuran (78 mL) were added to a clean dry 500 mL three neck round bottom flask, equipped with a nitrogen inlet, overhead stirrer and a cryogenic cooling bath. The resulting solution of diethyl oxalate was cooled to −60 to −78° C. and the tetrahydrofuran solution of 4-(3-magnesiobromopropyl)-1,3-dioxolane was added slowly maintaining the temperature in the range −60 to −78° C. The coupling reaction mixture was stirred at −60 to −78° C. for about 2 hours until the coupling reaction was judged to be complete by in-process GC analysis (the level of unreacted diethyl oxalate changes by NMT 0.5% in consecutive assays). The coupling reaction mixture at −60 to −78° C. was rapidly charged to a chilled (0–5° C.), agitated, biphasic mixture of methyl tertiary butyl ether (100 mL) and 12.5 w/v % aqueous citric acid. The phases were separated and the aqueous layer was extracted with methyl tertiary butyl ether (100 mL). The combined organic layers were washed with a pH 6.5 to 7.0, 10 w/v % sodium dihydrogen phosphate buffer (100 mL). The resulting methyl tertiary butyl ether solution of Methyl-5-(1,3-dioxolan-2-yl)-2-oxo-pentanoate was cooled to 0 to 5° C. and a lithium hydroxide solution (85 mL, 9.90 g lithium hydroxide monohydrate in 80 mL of water) was added maintaining the temperature at <5° C. The biphasic reaction mixture was stirred at 0 to 10° C. until the saponification was judged to be complete by in-process GC analysis (<1 relative area % vs the T=0 sample). Following complete reaction the phases were separated and the organic layer was extracted with water (10 mL). The combined aqueous phases were warmed to 15 to 30° C. and diluted with isopropanol (800 mL) over no less than 20 minutes. The resulting crystal slurry was agitated at 15 to 30° C. for about 1 hour and was then cooled to 0–5° C. and stirred until the product concentration in the supernatant was less than 8 M %. The lithium-5-(1,3-dioxolan-2-yl)-2-oxo-pentanoate was collected on a filter and the wet-cake was washed with cold (0–5° C.) aqueous isopropanol (1:8, 75 mL). The wet-cake was dried in vacuo at 40–50° C. to afford lithium-5-(1,3-dioxolan-2-yl)-2-oxo-pentanoate as white free-flowing crystals (34.0 g, 68.0 M %, HPLC Retention time=4.0 min, HPLC AP=94%).

HPLC method: Column; YMC basic 5 micon particle size, 4.6×250 mm, solvent; 10:90 Acetonitrile:0.01 M ammonium acetate, flow rate=1 mL/m, and detection is UV@210 nm.

Analytical data: $^1$H-NMR: 300 MHz: $D_2O$: δ1.5–1.6 (m, 4H), 2.65 (tr, 2H), 3.7–3.9 (m, 4H) and 4.8 (tr, 1H). $^{13}$C-NMR: 75 MHz: $D_2O$: δ17.62, 33.39, 39.17, 64.97, 114.26, 171.86 and 206.99.

EXAMPLE 10

The following process description details the procedure used for isolating 5-(1,3-dioxolan-2-yl)-(S)-2-amino-pentanoic acid from the enzymatic reductive amination process streams after ultrafiltration through a 10,000 MW limit filter.

Isolation of 5-(1,3-dioxolan-2-yl)-(S)-2-amino-pentanoic acid

In aqueous solution of (S)-a-Amino-1,3-dioxolane-2-pentanoic acid concentration=16 g/L, 3500 mL volume) which is contaminated with oxalic acid (concentration=7.74 mM) was sparged with nitrogen. The pH of the solution was adjusted from 8.6 to about 6.5 by the addition of 30 w/v % acetic acid (55 mL) and sparging with nitrogen was discontinued. Following pH adjustment, 1 M calcium chloride solution (81.4 mL) was added to the neutralized product solution based on the level of contamination with oxalic acid. The resulting slurry was stirred at room temperature for 20–30 minutes, at 60° C. for 30–60 minutes and was concentrated in vacuo at ~50° C. to 900 mL. The resulting slurry was filtered, the filtrate was tested for residual oxalic acid (Sigma kit 591) and was concentrated in vacuo further to 350 mL. With agitation, methanol (1400 mL) was added to the concentrate and the resulting mixture was heated at 55–60° C. for about 1 hour. The resulting crystal slurry was cooled to 1–5° C. over 1–1.5 hours and held at that temperature for 2–4 hours. The product crystals were collected on a filter, washed with cold methanol and dried in vacuo at 40–50° C., until the LOD was less than 1% to afford 5-(1,3-dioxolan-2-yl)-(S)-2-amino-pentanoic acid (44.7 g, 78.5% recovery, 97.7% potency vs std, HPLC AP=98.9%, HPLC retention time=2.7 minutes, residual R enantiomer=ne (not evident)) as white crystals.

HPLC method: Column: YMC ODS AQ 4×50 mm, solvent; copper sulfate pentahydrate, 782 mg/L in water, flow rate=1 mL/m, and detection is UV@230 nm, retention time=2.7 minutes.

EXAMPLE 11

The following process description details the procedure used to prepare 17.4 g (80.8 M %) of (S)-2-Amino-6,6-dimethoxyhexanoic acid, methyl ester from 20.0 g of 5-(1,3-dioxolan-2-yl)-(S)-2-amino-pentanoic acid.

Preparation of (S)-2-Amino-6,6-dimethoxyhexanoic acid, methyl ester

Under nitrogen, chlorotrimethyl silane (28.0 g) was added to a slurry of 5-(1,3-dioxolan-2-yl)-(S)-2-amino-pentanoic acid (20.0 g) and dimethyl sulfite (12.0 g) in methanol (240 mL) to afford a homogeneous solution. Following the observation of an exotherm to 29° C., the solution was heated to 40–45° C., stirred at that temperature for 8 h and at ~22° C. for up to 72 hours. In-process HPLC analysis showed that the reaction was complete (~93 M % conversion to product) and the resulting solution was cooled to −5 to −10° C. With stirring, the apparent pH of the mixture was adjusted to 11.7 to 11.9 by the slow careful addition of 32% (or 4.45 M) methanolic potassium methoxide solution (70 mL) maintaining the temperature in the range −5 to 0° C. Analysis of the product slurry (NMR) indicated that the neutralization was complete (chemical shift of the alpha proton of BMS-205787 was <3.36 ppm). The solvent of the product slurry was exchanged with ethyl acetate by first concentrating the thin slurry under vacuum at <30° C. to 300 mL volume followed by the addition of ethyl acetate until the removal of methanol was completed as judged by in-process GC analysis (<1 AP). Upon completion of the solvent exchange, the batch volume was adjusted to ~400 mL with ethyl acetate and the resulting slurry was filtered. Poly(acrylic acid co-acrylamide), potassium salt (3.0 to 3.2 g) and water (30–32 mL) were added to the filtrate. The mixture was stirred for ~35 minutes and filtered. Optionally, the Poly (acrylic acid co-acrylamide), potassium salt treatment can be repeated on the filtrate if the quantity of ethylene glycol exceeds 0.15 equivalents, as judged by in-process GC analysis. Following in-process HPLC analysis, (S)-2-Amino-6,6-dimethoxyhexanoic acid, methyl ester (17.4 g) was obtained as an ethyl acetate solution in 80.8 M % yield.

Analytical data: HPLC: Tr=7.1 min (UV 215): Mac-Mod Analytical, Zorbax CN 5 micro M, 4.6×250 mm, 72 v/v % (0.02 M ammonium phosphate solution): 28 v/v % acetonitrile, 20 micro L injection volume eluted at 1.0 mL/min. Dilute 300 micro L to 5 mL with mobile phase.

EXAMPLE 12

The following process description details the procedure used to prepare 62.5 g (78.7 M %) of (S)-2-Amino-6,6-dimethoxyhexanoic acid, methyl ester oxalic acid salt (1:1) from 50 g of 5-(1,3-dioxolan-2-yl)-(S)-2-amino-pentanoic acid.

Preparation of (S)-2-Amino-6,6-dimethoxyhexanoic acid, methyl ester oxalic acid salt (1:1)

To a 250 mL, 3 neck flask equipped with a mechanical agitator, thermocouple, heating mantle, condenser, nitrogen inlet and vent, (5-(1,3-dioxolan-2-yl)-(S)-2-amino-pentanoic acid (50 g), methanol (300 mL) and dimethyl sulfite (11.2 mL) were charged. Chlorotrimethyl silane (83.9 mL) was added to the resulting slurry and the reaction mixture was heated at 40 to 42° C. for about 8 hours, followed by stirring at ambient temperature for eight hours. Potassium bicarbonate (104.3 g) was slurried in methanol (200 mL) contained in a 2-L three neck flask and the reaction mixture containing the hydrochloride salt of (S)-2-Amino-6,6-dimethoxyhexanoic acid, methyl ester was neutralized by adding it to the potassium bicarbonate slurry maintaining the pH of mixture above 7. Hyflo (12.5 g) and n-butyl acetate (400 mL) were added and the mixture was concentrated under vacuum (76 to 180 mmHg) to remove methanol maintaining the temperature of the mixture below 30° C. tert-Butyl methyl ether (300 mL) was added to the slurry and after cooling to −5° C., the salts of neutralization were removed by filtration and the filter cake was washed with tert-Butyl methyl ether (50 mL). The combined filtrates were warmed to 20 to 25° C. and a warm (~27° C.) methanolic (73 mL) solution of oxalic acid dihydrate (36.7 g) was added portion wise over about 1 hour. The resulting slurry of (S)-2-Amino-6,6-dimethoxyhexanoic acid, methyl ester oxalic acid salt (1:1) was agitated for 30 minutes and additional product was crystallized by the slow addition of tert-butyl methyl ether (800 mL). After stirring the product slurry for 30 minutes, it was cooled to 0 to 5° C., held for at least 1 hour, and filtered. The wet-cake was washed with tert-butyl methyl ether (2×300 mL) and dried under vacuum (~200 mm Hg) at no more than 40° C. The product, (S)-2-Amino-6,6-dimethoxyhexanoic acid, methyl ester oxalic acid salt (1:1) (62.5 g), was isolated as a white free flowing powder in 78.7 M % corrected yield from (S)-2-Amino-6,6-dimethoxyhexanoic acid, methyl ester, having an HPLC AP of 97.0 and a free base potency (vs. lab standard) of 68.3%.

Analytical data: HPLC: Tr=13.5 min (UV 205 nm): Rockland Technologies Inc., Zorbax CN 5 micro M, 4.6× 250 mm (product #880952.705), 85 v/v % (0.01 M potassium phosphate solution): 15 v/v % acetonitrile, 10 micro L injection volume eluted at 1.0 mL/min. The HPLC response was found to be linear in the range of 0.16 to 1.5 mg/mL. Samples may be diluted with methanol or mobile phase.

Analytical data: $^1$H-NMR: 300 MHz: $CD_3OD$: δ1.3–1.6 (m, 4H), 1.8–2.0 (m, 2H), 3.3 (s, 6H), 3.8 (s, 3H), 4.1 (tr, 1H), 4.4 (tr, 1H) and 5.1 (br s, 3H). $^{13}$C-NMR: 75 MHz: $CD_3OD$: δ21.03, 31.29, 33.06, 53.56, 53.65, 53.89, 105.74, 166.49 and 171.14.

EXAMPLE 13

The following process description details the procedure used to prepare 100.3 g (78 M % corrected) of (S)-2-Amino-6,6-dimethoxyhexanoic acid, methyl ester oxalic acid salt (2:1) from 100 g of 5-(1,3-dioxolan-2-yl)-(S)-2-amino-pentanoic acid.

Preparation of (S)-2-Amino-6,6-dimethoxyhexanoic acid, methyl ester oxalic acid salt (2:1)

To a 250 mL, 3 neck flask equipped with a mechanical agitator, thermocouple, heating mantle, condenser, nitrogen inlet and vent, 5-(1,3-dioxolan-2-yl)-(S)-2-amino-pentanoic acid (100 g), methanol (1200 mL) and dimethyl sulfite (44.8 mL) were charged. Chlorotrimethyl silane (168 mL) was added to the resulting slurry and the reaction mixture was heated at 40 to 42° C. for about 8 hours, followed by stirring at ambient temperature for eight hours to afford a solution of (S)-2-Amino-6,6-dimethoxyhexanoic acid, methyl ester hydrochloride salt (in-process quantitation 100.9 g, 93 M %). Potassium bicarbonate (208.6 g) as slurried in methanol (400 mL) contained in a 5-L three neck flask and the reaction mixture containing the hydrochloride salt of (S)-2-Amino-6,6-dimethoxyhexanoic acid, methyl ester, was neutralized by adding it to the potassium bicarbonate slurry (over 1.5 hours) maintaining the pH of mixture above 6.9. The solvent of the resulting slurry was replaced with n-butyl acetate by vacuum distillation (50 to 60 mmHg and 30 to 40° C.) maintaining a pot volume of about 2 L. After 2.25 L of n-butyl acetate was distilled, methanol (1.25 L) was added to the distillation vessel and the distillation was continued, maintaining a pot volume of NLT 2 L, until the water content of the slurry supernatant was <0.05 wt % and the methanol level was <5 relative area %. Hexane (1.5 L) was charged to the resulting slurry and it was then cooled to −5° C. After stirring the mixture for 1 hour, it was filtered and the filter-cake was washed with hexane (2×100 mL). The resulting hazy filtrate was polish filtered to afford a clear filtrate. The clear filtrate was warmed to 20 to 25° C. and a methanolic (1333 mL) solution of oxalic acid dihydrate (33.3 g) was added slowly over about 2 hours. The resulting slurry of (S)-2-Amino-6,6-dimethoxyhexanoic acid, methyl ester oxalic acid salt (2:1) was agitated for 18 hours at ambient temperature and the product was collected on a filter. The product wet-cake was washed with acetonitrile (4×100 mL) and dried under vacuum at 45° C. to afford 103.2 g (78 M %) of (S)-2-Amino-6,6-dimethoxyhexanoic acid, methyl ester oxalic acid salt (2:1) having a free base potency of 84 wt % (vs. lab standard, theo.=82 wt %) and an HPLC AP of 100.

Analytical data: HPLC: Tr=10.0 min (UV 205 nm): Rockland Technologies Inc., Zorbax stable bond CN. 5 micro-M, 4.6×250 mm, 85 v/v % (0.01 M potassium dihydrogen phosphate solution adjusted to pH 7.5 with KOH): 15 v/v % acetonitrile, 10 micro L injection volume eluted at 1.0 mL/min. Samples may be diluted with methanol or mobile phase.

Analytical data: ¹H-NMR: 300 MHz: $D_6DMSO\delta$ 1.2–1.4 (m, 2H), 1.4–1.6 (m, 2H), 1.6–1.8 (m, 2H), 3.2 (s, 6H), 3.55 (tr, 1H), 3.7 (s, 3H), 4.3 (tr, 1H) and 5.9 (br s, 4H). ¹³C-NMR: 75 MHz: $D_6DMSO$: δ 21.00, 31.77, 32.08, 52.04, 52.39, 52.85, 103.75, 165.01 and 173.09.

EXAMPLE 14

The following process description details the procedure used to prepare 60.3 g (80 M % as is of 5-(1,3-dioxolan-2-yl)-2-oxo-pentanoic acid from 110 g of 4-(3-bromopropyl)-1,3-dioxolane.

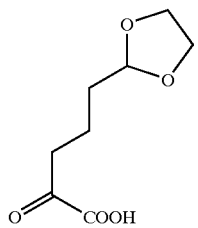

To a 500 mL 3-necked round bottom flask equipped with a dropping funnel, nitrogen line, overhead stirrer, thermocouple, and water bath, magnesium turnings (14.13 g) were charged. Under a nitrogen atmosphere, the magnesium turnings were rinsed with dry tetrahydrofuran (KF= 0.0016 wt %, 3×70 mL). The flask was charged with tetrahydrofuran (70 mL, KF=0.02 wt %) followed by 5 mL of an ca. 2 M tetrahydrofuran solution of pre-formed Grignard reagent in tetrahydrofuran. The dropping funnel was charged with a neat mixture of 85:15 bromoacetal:chloroacetal (110 g, 90:10 wt %). After approximately 0.5 mL of the bromoacetal mixture was added to the reaction flask, the temperature increased from 20° C. to 25° C. The rate of addition was adjusted to maintain a reaction temperature of about 30° C. The addition funnel was rinsed with tetrahydrofuran (25 mL), and the rinse was added to the reaction flask. The addition was complete after ca. 1.5 hours and the batch was allowed to cool to room temperature. At this point in-process GC analysis of the Grignard reagent indicated that 90% of the bromoacetal had converted to the Grignard reagent with no cyclobutane impurity, while the chloroacetal did not appear to react.

A 1 L 3-necked round bottom flask was equipped with a nitrogen line, overhead stirrer, and thermocouple. Under a nitrogen atmosphere, the flask was charged with diethyl oxalate (73.85 g) and tetrahydrofuran (250 mL). The solution was cooled to −60° C., and the liquid portion of the Grignard reagent was added to the cooled diethyl oxalate solution via cannula to maintain the temperature below −55° C. The Grignard preparation flask was washed with tetrahydrofuran (3×20 mL), and the resulting wash was added via cannula. The addition was complete after 1.5 hours, and the reaction was stirred for about 2 hours at −60° C. to −55° C. The cold reaction mixture was immediately poured into a mixture consisting of $NH_4Cl$ (32.1 g), water (100 mL), ice (200 g) and ethyl acetate (300 mL). The layers were separated and the aqueous layer was extracted again with ethyl acetate (2×300 mL). The combined organic layers were dried over magnesium sulfate and concentrated to afford 87 g (79 M % yield) of 5-(1,3-dioxolan-2-yl)-2-oxo-pentanoic acid, ethyl ester as a thick liquid.

A 3 L 3-necked round bottom flask was equipped with an overhead stirrer, thermocouple, and an addition funnel containing 1.5 N NaOH (460 mL). The flask was charged with MeOH (700 mL) and cooled to 0° C. The NaOH solution was added slowly to the methanol, maintaining the temperature below 10° C. and upon complete addition, the resulting solution was cooled to 0° C. A methanol solution of 5-(1,3-dioxolan-2-yl)-2-oxo-pentanoic acid, ethyl ester (350 mL) was added to the reaction via dropping funnel at a rate which maintained the temperature of the reaction mixture below 3° C. (addition time 1 hr). The reaction was stirred at 0° C. for 2 hours and the pH of the reaction was adjusted to 7.71 by the addition of 2 M potassium bisulfate (75 mL). The methanol was evaporated and the cloudy aqueous slurry was washed with MTBE (3×500 mL). The pH of the aqueous layer was adjusted to 4.5 by the addition of 2 M potassium bisulfate (100 mL) and extracted with ethyl acetate (500 mL). The pH of the aqueous layer was further adjusted to 2.0 by the addition of 2 M potassium bisulfate (50 mL), and extracted with ethyl acetate (2×500 mL). The combined ethyl acetate extracts were dried over magnesium sulfate and concentrated to afford 5-(1,3-dioxolan-2-yl)-2-oxo-pentanoic acid (60 g, 80 M % yield) as a thick liquid.

(5-(1,3-dioxolan-2-yl)-2-oxo-pentanoic acid)-¹H-NMR: 300 MHz: $CDCl_3$: δ 1.75 (br m, 4H), 2.95 (tr, 2H), 3.85 (m, 2H), 3.95 (m, 2H), 4.85 (tr, 1H) and 7.70 (br s, 1H). ¹³C-NMR: 75 MHz: $CDCl_3$: δ 17.27, 32.30, 37.19, 64.85, 103.94, 160.19 and 195.38.

Scheme 4 depicts the reaction in examples 15 and 16.

Scheme 4

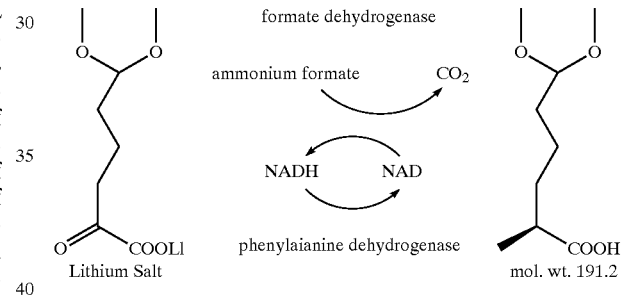

EXAMPLE 15

Ammonium formate (175 mg, 2.775 mmoles), 6,6-dimethoxy-2-oxohexanoic acid, monolithium salt (50 mg, 0.255 mmoles), 10 ml water, dithiothreitol (1.64 mg, 10.6 μmoles), NAD (7.05 mg, 10.3 μmoles), heat-dried *E. coli* containing cloned phenylalanine dehydrogenase from *Thermoactinomyces intermedius* (50 mg, 62.5 units), and heat-dried *Candida boidinii* (82.55 mg, 2.75 units) were added to a 50 ml Erlenmeyer flask in that order. The pH was 8.03 without adjustment. The flask was shaken at 40° C., 200 rpm for 18 h. A Chiralpak WH column (Daicel Chemical Industries) was used to estimate the concentration of the product (S)-2-amino-6,6-dimethoxyhexanoic acid by the same method described for 5-(1,3-dioxolan-2-yl)-(S)-2-amino-pentanoic acid. No standards are available for the enantiomers, but this material is presumably the S-amino acid. The molar yield of amino acid was estimated to be 74.5%. (5-(1,3-dioxolan-2-yl)-S-2-amino-pentanoic acid was used as an HPLC standard to estimate concentration). MS: $(M+H)^+$, 192.

EXAMPLE 16

Ammonium formate (389.8 mg, 6.18 mmoles), 6,6-dimethoxy-2-oxohexanoic acid, monolithium salt (1.000 g, 5.099 mmoles), 20 ml water, dithiothreitol (3.28 mg, 21.27

μmoles), NAD (14.1 mg, 20.57 μmoles), Pichia wet cells stored frozen (0.2255 g containing 5.5 u formate dehydrogenase and 34.7 units phenylalanine dehydrogenase from *Thermoactinomyces intermedius*) were added to a 50 ml Erlenmeyer flask in that order. The pH was adjusted from 7.56 to 8.0 with NH$_4$OH. The flask was shaken at 40° C., 200 rpm for 43 h. After the reaction, the cells were removed by centrifugation and the supernatant was then ultrafiltered with a 10,000 MW cutoff polysulfone membrane (YM10). The corrected overall yield of (S)-2-amino-6,6-dimethoxyhexanoic acid from reaction initiation to after cell and protein removal was estimated with a Chiralpak WH column as 108%.

EXAMPLE 17

The following process description details the procedure used to prepare 4.33 g (25 M % as is of 6,6-dimethoxy-2-oxo-hexanoic acid) from 10 g of 4,4-dimethoxy-1-bromobutane.

To a 100 mL 3-necked round bottom flask equipped with a dropping funnel, nitrogen line, overhead stirrer, thermocouple, and water bath, magnesium turnings (1.7 g) were charged. Under a nitrogen atmosphere, the magnesium turnings were rinsed with dry tetrahydrofuran (10 mL). The flask was charged with tetrahydrofuran (6 mL, KF=0.02 wt %) followed by 1 mL of a pre-formed Grignard reagent in tetrahydrofuran (4,4-dimethoxy-1-magnesiobromobutane). The dropping funnel was charged with a THF solution of 4,4-dimethoxy-1-bromobutane (10 g, in 26 mL of THF). The solution was added dropwise, while maintaining the temperature between 28 and 31° C. After the addition was completed, the solution was held at 30° C. for 1 hour.

A 100 mL 3-necked round bottom flask equipped with a nitrogen line, overhead stirrer, and thermocouple was rinsed with 20 mL of anhydrous THF. Diethyloxalate (4.85 g) and THF (10 mL) were charged to the flask and the solution was cooled to −70° C. The THF solution of the Grignard reagent (4,4-dimethoxy-1-magnesiobromobutane) was charged to the diethyloxalate solution maintaining the temperature between −60 and −70° C. The reaction mixture was held at −70° C. for 2 hours, when it was judged complete by in-process GC analysis (0.5% unreacted diethyloxalate). The reaction mixture was quenched by pouring it into a solution of citric acid (5 g citric acid dissolved in 40 mL of water). The quenched reaction mixture was extracted with methyl tertiary butyl ether (2×20 mL) and the combined methyl tertiary butyl ether extracts were washed with a solution of pH 6.5 monobasic sodium phosphate (2 g in 20 mL of water, pH adjusted with 10 N sodium hydroxide solution). The rich organic phase was cooled to 2° C. and a lithium hydroxide solution (1.4 g of LiOH in 15 mL water) was added dropwise maintaining the temperature below 5° C. The reaction mixture was stirred for 30 minutes at 5° C. until in-process GC analysis indicated that the reaction was complete (<0.5% unreacted ester in the organic phase). The phases were separated and the organic phase was extracted with water (2 mL). Isopropanol (300 mL was added to the rich aqueous phase and the resulting slurry was concentrated to a solid on a rotary evaporator. The solids were suspended in a mixture of methyl tertiary butyl ether (300 mL) and isopropanol (100 mL), the slurry was stirred at 3° C. for 1 hour and the product was collected on a filter. The product wet-cake was washed with cold methyl tertiary butyl ether/isopropanol (75 mL, 4:1, respectively) and dried under vacuum to afford lithium-6,6-dimethoxy-2-oxo-hexanoate (4.33 g, 25 M % from 4,4-dimethoxy-bromobutane).

Analytical data: HPLC: Tr=4.4 min (UV 210 nm): YMC-basic, 5 micro-M, 4.6×250 mm, 90 v/v % (0.05 M ammonium acetate solution): 10 v/v % acetonitrile, 10 micro L injection volume eluted at 1.0 mL/min.

Analytical data: $^1$H-NMR: 300 MHz: D$_2$O: δ 1.6 (br m, 6H), 3.3 (s, 6H), and 4.4 (m, 1H). $^{13}$C-NMR: 75 MHz: D$_2$O: δ 18.78, 32.39, 39.70, 54.34, 105.85, and 207.03.

EXAMPLE 18

The following process description details the procedure used for isolating (S)-2-Amino-6,6-dimethoxyhexanoic acid from the enzymatic reductive amination process stream after ultrafiltration through a 10,000 MW limit filter.

Isolation of (S)-2-Amino-6,6-dimethoxyhexanoic acid

An aqueous solution of (S)-2-Amino-6,6-dimethoxyhexanoic acid (concentration=26.5 g/L, 35 mL volume) which was contaminated with oxalic acid (concentration=5.4 mM) was sparged with nitrogen. The pH of the solution was adjusted to about 6.5 by the addition of 30 w/v % acetic acid (1.2 mL) and sparging with nitrogen was discontinued. Following pH adjustment, 1M calcium chloride solution (1.3 mL) was added to the neutralized product solution based on the level of contamination with oxalic acid. The resulting slurry was stirred at room temperature for 20–30 minutes, at 55° C. for 30 minutes and was filtered to remove calcium oxalate. The filtrate was stirred with Darco G-60 for 30 minutes and was filtered through HyFlo. The filtrate was concentrated in vacuo using n-buOH to remove water azeotropically, affording a foam (2.04 g). The foam was dissolved in methanol (5.1 mL) and mixed with acetonitrile (15 mL). The solution was seeded with (S)-2-Amino-6,6-dimethoxyhexanoic acid and cooled in an ice bath for 4 hours. The product was collected on a filter and the wet-cake was dried under vacuum at 50° C. for 4 hours to afford (S)-2-Amino-6,6-dimethoxyhexanoic acid (0.392 g, 35.6 M % from the input solution), HPLC area percent= 97.6).

Analytical data: HPLC: Tr=3.6 min (UV 230 nm): YMC-ODS AQ, 4.6×50 mm, anhydrous copper sulfate@500 mg/L concentration, 10 micro L injection volume eluted at 1.0 mL/min.

Analytical data: $^1$H-NMR: 300 MHz: D$_2$O: δ 1.3–1.5 (m, 2H), 1.6–1.75 (m, 2H), 1.8–2.0 (m, 2H), 3.4 (s, 6H), 3.75 (tr, 1H) and 4.6 (tr, 1H), 13C-NMR: 75 MHz: D$_2$O: δ 19.89, 30.57, 32.05, 53.82, 55.11, 105.07 and 175.05.

EXAMPLE 19

Dual Constitutive Expression of FDH and PDH

1. Construction of recombinant strain *Pichia pastoris* GS115 (pGAPZ-FDH)

pGAPZ is a vector obtained from Invitrogen (Carlsbad, Calif.). It permits expression of foreign genes in *P. pastoris* under control of the constitutive glyceraldehyde 3'-phosphate promoter. The formate dehydrogenase (fdh) gene from *Candida boidinii* was cloned into pGAPZ as follows:

The DNA sequence of the cloned *C. boidinii fdh* gene was determined and used to created oligonucleotide primers for its amplification using the polymerase chain reaction (PCR). The primers were (NH$_2$ terminus) 5'-GGAATTCCATATGAAGATCGTTTTAGTCTTA'3' (SEQ.ID.No.:1) and (COOH terminus) 5'-CCTTAAGAATAATAAAGAATAGACAAATGG-3' (SEQ.ID.No.:2). *C. boidinii* chromosomal DNA was used as target in the PCR reaction. The PCR reaction yielded a single DNA fragment of the expected size (ca. 1100-base pairs) which was isolated, purified, and cleaved with restriction endonuclease EcoRI. The digested PCR product was ligated with EcoRI-treated pGAPZ DNA and the ligation mix was transformed by electroporation into *E. coli* strain TOP 10 F'. Transformed cells were selected on LB agar medium containing 25 mg/ml of the antibiotic Zeocin (Invitrogen). Eighteen colonies were tested for the presence of the fdh gene by PCR; three were positive. The fdh gene was sequenced and determined to be the same as disclosed by Sakai, Y., et al. *J. of Bacteriology*, 179 pp. 4480–4485 (1997). One colony containing plasmid pGAPZ-FDH was chosen for further use. Plasmid DNA was isolated from TOP 10 F'(pGAPZ-FDH), linearized with restriction endonuclease AvrII, and electroporated into *P. pastoris* GS115. Transformants containing multiple integrated copies of pGAPZ-FDH were selected by spreading the cells onto medium containing 2 g/l Zeocin. Several such colonies were obtained and found to possess at least twice the FDH activity of cells containing only pGAPZ (*P. pastoris* contains its own FDH gene). The isolate giving the highest specific FDH activity was chosen for further work and designated GS115 (pGAPZ-FDH).

2. Construction of pGAPk-PDH

The next step in the construction of the dual constitutive expression strain was the introduction of a recombinant phenylalanine dehydrogenase (pdh) gene into GS115 (pGAPZ-FDH). Since this strain was already Zeocin-resistant, a plasmid containing the constitutive promoter but permitting an alternative means of selection for transformants was created. A 546-base pair BglII/NotI restriction fragment of pGAPZ which contained the glyceraldehyde 3'-phosphate promoter region was cloned into a 9000-base pair BamHI/NotI fragment of pPIC9k (Invitrogen). The new plasmid was named pGAPk. pGAPk allows selection of transformants on minimal medium due to the presence of a functional HIS4 gene which complements a defective version present in GS115. Multiple integrants can be selected using resistance to antibiotic G418, also encoded by the plasmid. A map of pGAPk is attached.

3. Construction of recombinant plasmid pGAPk-PDH and transformation of GS115(pGAPZ-FDH)

Using the published DNA sequence of the *Thermoactinomyces intermedius* phenylalanine dehydrogenase gene (Takada, H., et al., *J. of Biochem.*, 109, pp. 371–376 (1991)), DNA primers corresponding to the $NH_2$ (5'-CGGAATTCAAGATGCGCGACGTGTTTGAAATG-3') (SEQ.ID.No.:3) and COOH (5'-CGTTCTCGCGTTCCTCCATTGAGCTCGCC-3') (SEQ.ID.No.:4) terminii were synthesized. They were used for PCR with *T. intermedius* chromosomal DNA as target DNA. A fragment of the expected size (ca. 1100-base pairs) was seen after agarose gel electrophoresis. The DNA was purified and digested with restriction endonucleases EcoRI and XhoI. pGAPk was cleaved with EcoRI and then partially digested with XhoI: the 9500-base pair fragment was isolated following agarose gel electrophoresis. The two fragments were ligated together and transformed into *E. coli* DH10B cells by electroporation. Transformants were screened for the presence of the pdh gene by colony PCR. One such colony was identified and the plasmid named pGAPk-PDH.

pGAPk-PDH was linearized using restriction enzyme AvrII and electroporated into *P. pastoris* GS115(pGAPZ-FDH). Transformants were selected by their ability to grow on minimal glucose agar plates. Approximately 10,000 colonies were screened for resistance to G418 (4g11). Several resistant colonies were isolated and grown in liquid YPD medium, then harvested and assayed for PDH and FDH activity. Both activities were present. A use test for the bioconversion of 5-(1,3-dioxalan-2-yl)-2-oxo-pentanoic acid to 5-(1,3-dioxalan-2-yl)-(S)-2-amino pentanoic acid was positive using a cell extract from a recombinant isolate.

EXAMPLE 20 rPDH Inducible Expression Systems 1. rPDH expression by recombinant strain *E. coli* BL21 (DE3) (pPDH155K).

Figure 2:
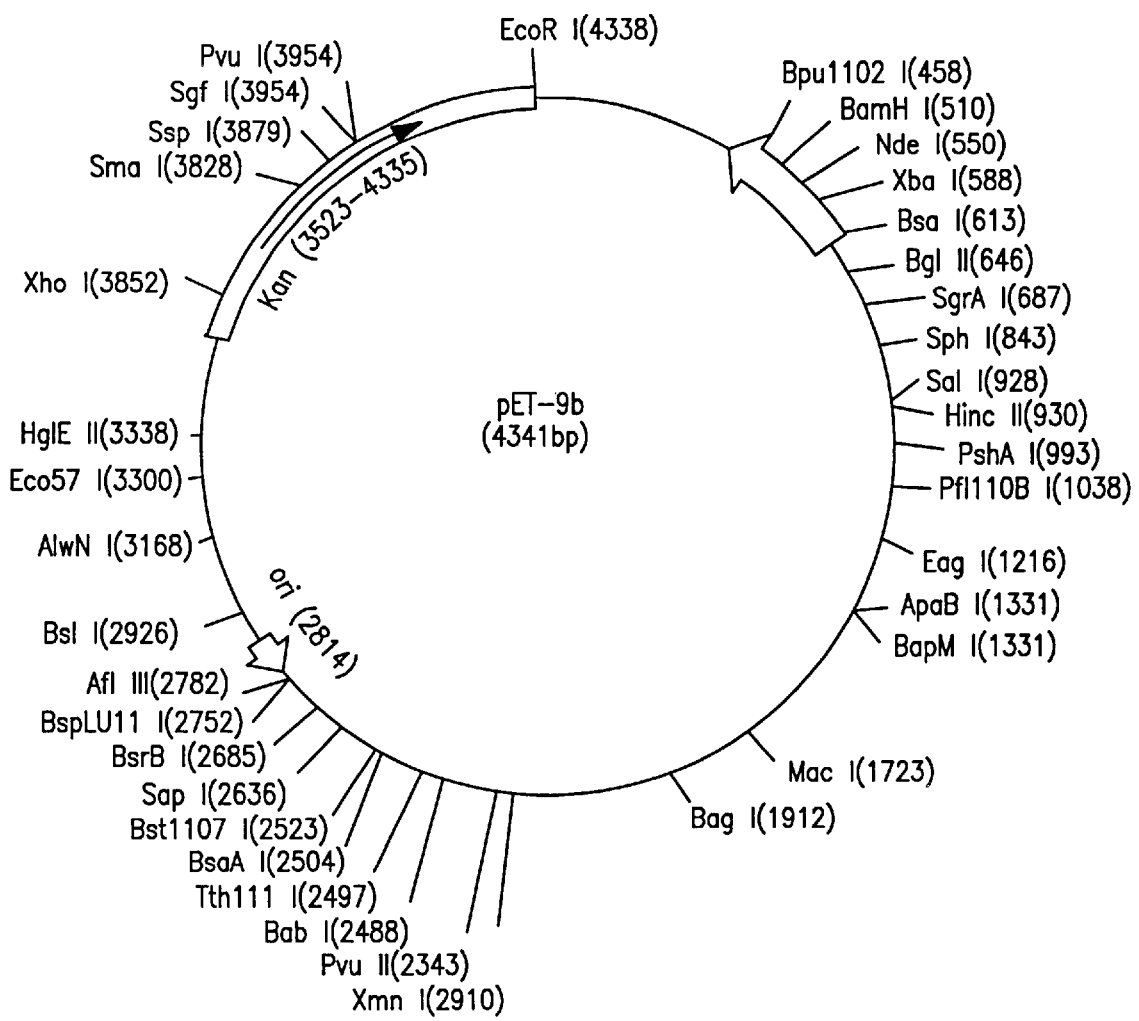
FIG. 2. Plasmid pET-9b.

Construction of the final recombinant vector (pPDH155K) was in two steps: a) the cloning of the *Thermoactinomyces intermedius* PDH gene into plasmid vector pET15b (Novagen, Madison, Wis.: FIG. 1) to make recombinant vector pPDH15b/1; and, b) exchange of the ampicillin resistance marker of plasmid vector pPDH15b/1 with the kanamycin resistance marker of vector pET9b (Novagen, Madison, Wis.: FIG. 2). Expression of the PDH gene in this system under the control of the strong T7 promoter. Induction of PDH expression is with IPTG (isopropyl B-D-thiogalactopyranoside). Expression of the PDH protein is intracellular.

Recombinant strain *E. coli* BL21(DE3) (pPDH155K) (ATCC 98374) was constructed in the following manner. Using published *T. intermedius* phenylalanine dehydrogenase (PDH) DNA sequence (Takada, et al., *J. of Biochem.*, 109, pp. 371–376 (1991)), DNA primers corresponding to the N-(5'CATGCCATGGTCGACGTGTTTGAAATGATGG3') (SEQ.ID.No.:5) and C-(5'CCGCTCGAGTTACCTCCTTGCGCTGTTGC3') (SEQ.ID.No.:6) termini of the PDH protein were synthesized and used in a PCR reaction using *T. intermedius* target DNA. The PCR reaction yielded a single DNA fragment of expected size which was isolated, purified and then digested with restriction enzymes NcoI and XhoI. The digested PCR fragment was ligated with NcoI/XhoI-digested pET15b plasmid vector, and the ligation mix transformed by electroporation into *E. coli* strain BL21(DE3). SDS-PAGE analysis of cell extracts from induced cultures of isolate *E. coli* BL21(DE3) (pPDH15b/1) demonstrated the presence of an overexpressed protein of correct size. PDH activity assays as well as use test for the bioconversion of 5-(1,3-dioxalan-2-yl)-2-oxo-pentanoic acid to 5-(1,3-dioxalan-2-yl)-(S)-2-amino-pentanoic acid were positive using the recombinant cell extracts.

Vector pPDH15b/1 was then isolated and digested with restriction enzymes AlwNI and EcoRI. Digestion of pPDH15b/1 with these two enzymes completely drops out the ampicillin resistance gene without affecting the PDH expression cassette or plasmid replication/maintenance functions. Likewise, plasmid vector pET9b was digested with the same two restriction enzymes, and the 1.17 kb AlwNI/EcoRI DNA fragment containing the kanamycin resistance gene was isolated and then used in a ligation reaction with the pPDH15b/1 PDH-containing fragment (described above). The ligation mix was used to transform by electroporation *E. coli* strain BL21(DE3). A kanamycin resistant transformant [*E. coli* BL21(DE3) (pPDH155K)] was isolated and verified by PCR for the presence of the PDH expression casette. PDH activity assays as well as use test for the bioconversion of 5-(1,3-dioxalan-2-yl)-2-oxo-pentanoic acid to 5-(1,3-dioxalan-2-yl)-(S)-2-aminopentanoic acid using cell lysates from this recombinant strain were positive.

2. FDH/rPDH expression by recombinant strain *Pichia pastoris* SMD1168 (pPDH9K/10).

Figure 3:
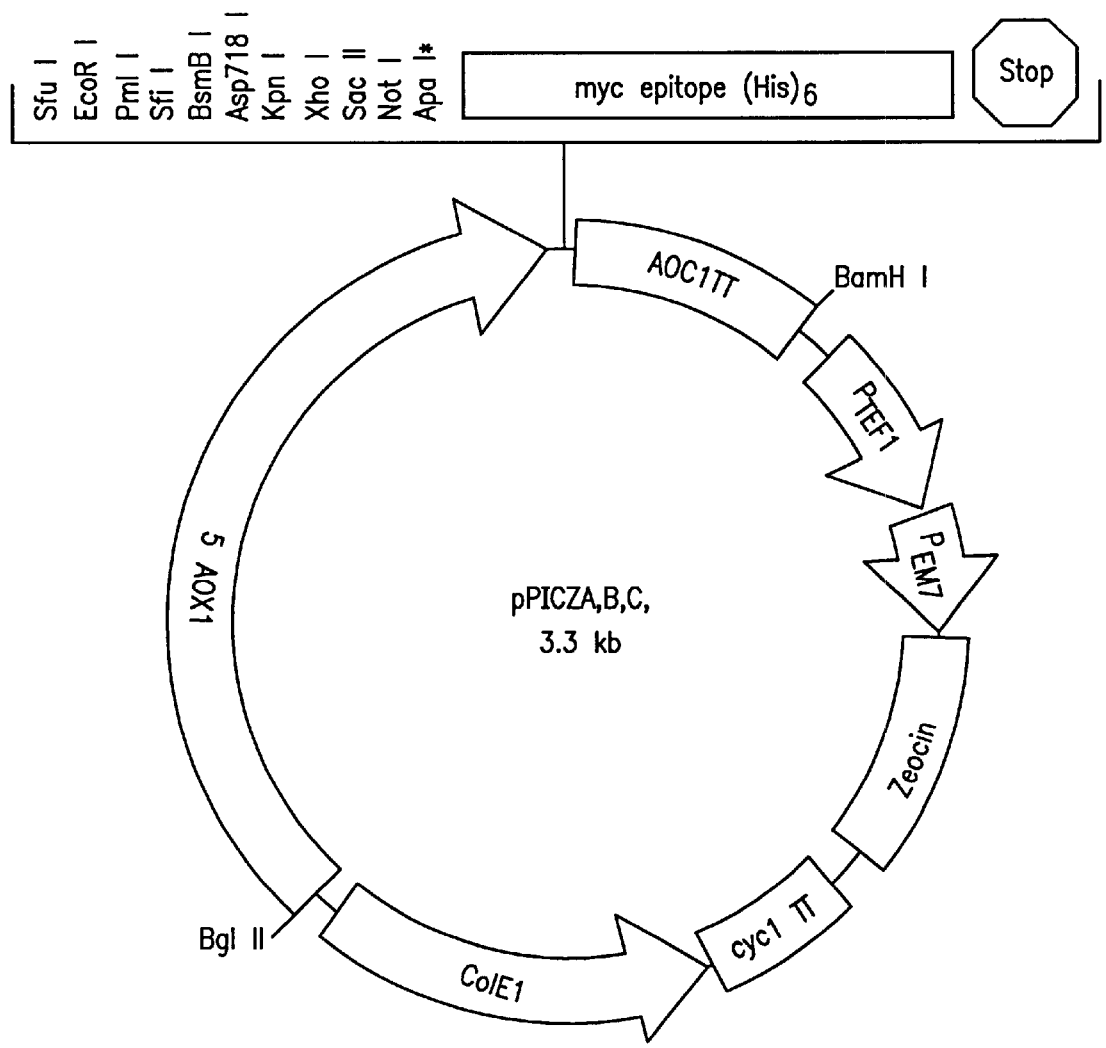
FIG. 3. Plasmid PPICZ A,B,C. Features include 5' AOX1 promoter region at 1-942; 5' end of AOX1 mRNA at 824; 5' AOX1 priming site at 855–875; Multiple cloning site at 932–1011; myc epitope tag at 1012–1044; polyhistidine tag at 1057–1077; 3' AOX priming site at 1160–1180; 3' end of mRNA at 1251. AOX1 transcription termination region at 1078–1419; fragment containing TEF1 promoter at 1420–1831; EM7 promoter at 1832–1899; Sh ble ORF at 1900–2274; CYC1 transcription termination region at 2275–2592; ColE1 origin at 2603–3276.
Figure 4:
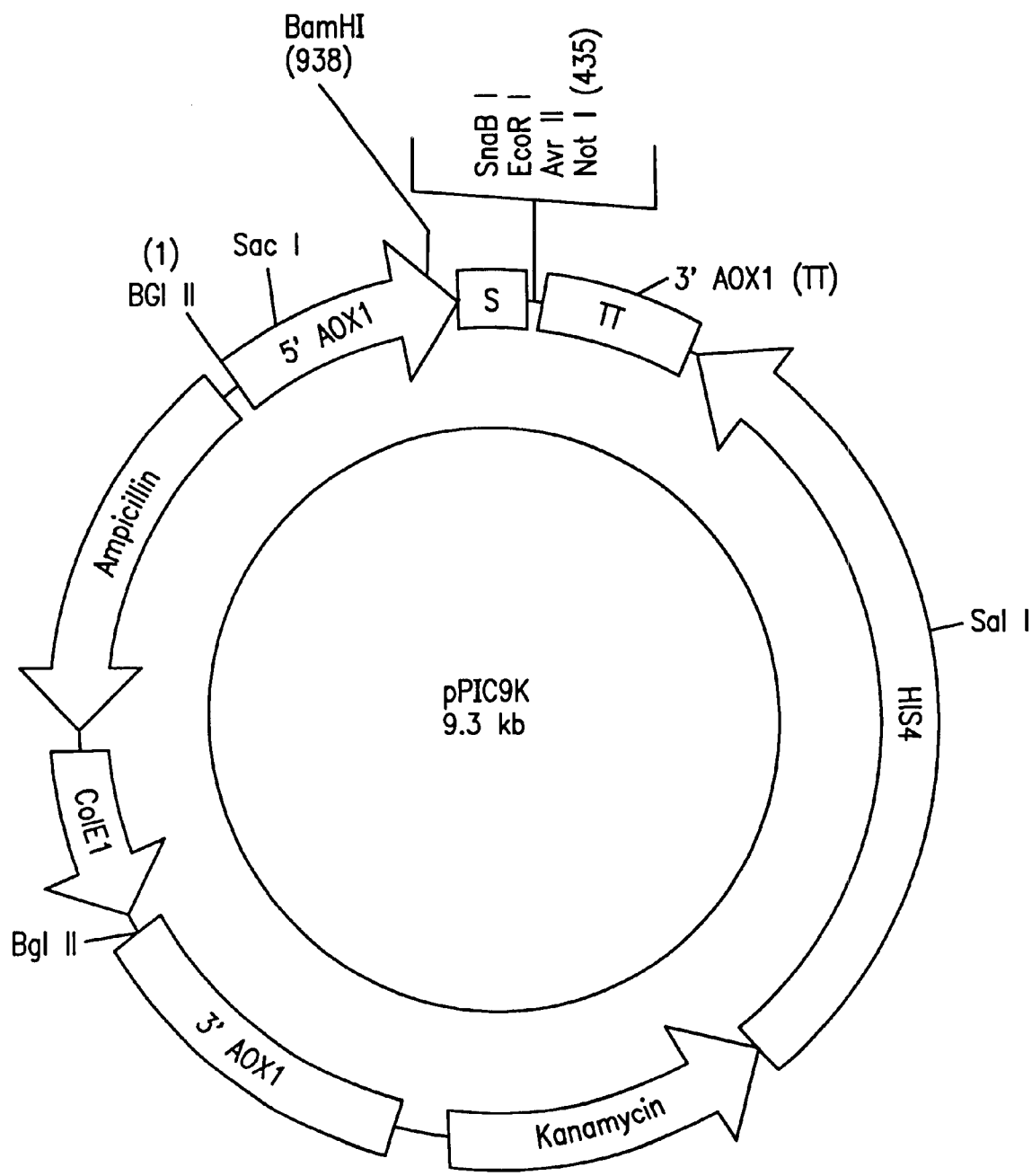
FIG. 4. Plasmid pPIC9k. Features include 5' AOX1 promoter fragment at 1-948; 5' AOX1 primer site at 855–875; alpha-factor secretion signal(s) at 949–1218; alpha-factor primer site at 1152–1172. Multiple cloning site at 1192–1241; 3' AOX1 primer site at 1327–1347; 3' AOX1 transcription termination region at 1253–1586; HIS4 ORF at 4514–1980; kanamycin resistance gene at 5743–4928; 3' AOX1 fragment at 6122–6879; ColE1 origin at 7961–7288; ampicillin resistance gene at 8966–8106.
Figure 5:
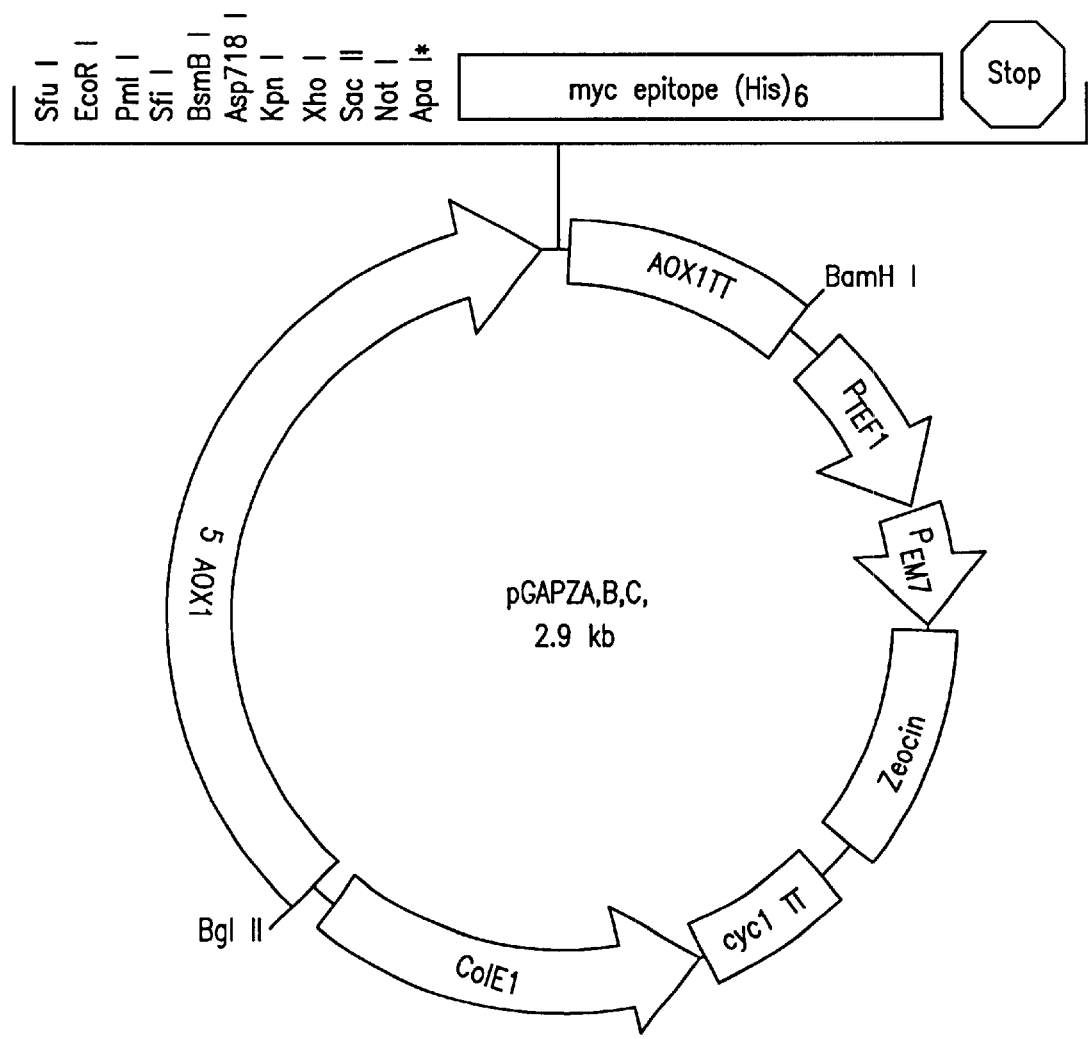
FIG. 5. Plasmid pGAPZ A,B,C. Features include GAP promoter region at 1-483; pGAP forward priming site at 455–476. Multiple cloning site at 484–563; myc epitope tag at 564–593; polyhistidine tag at 609–626; 3' AOX1 priming site at 711–731; AOX1 transcription termination region at 630–970; fragment containing TEF1 promoter at 971–1381; EM7 promoter at 1382–1449; Sh ble ORF at 1450–1824; CYC1 transcription termination region at 1825–2142; ColE1 origin at 2153–2826.
Figure 6:
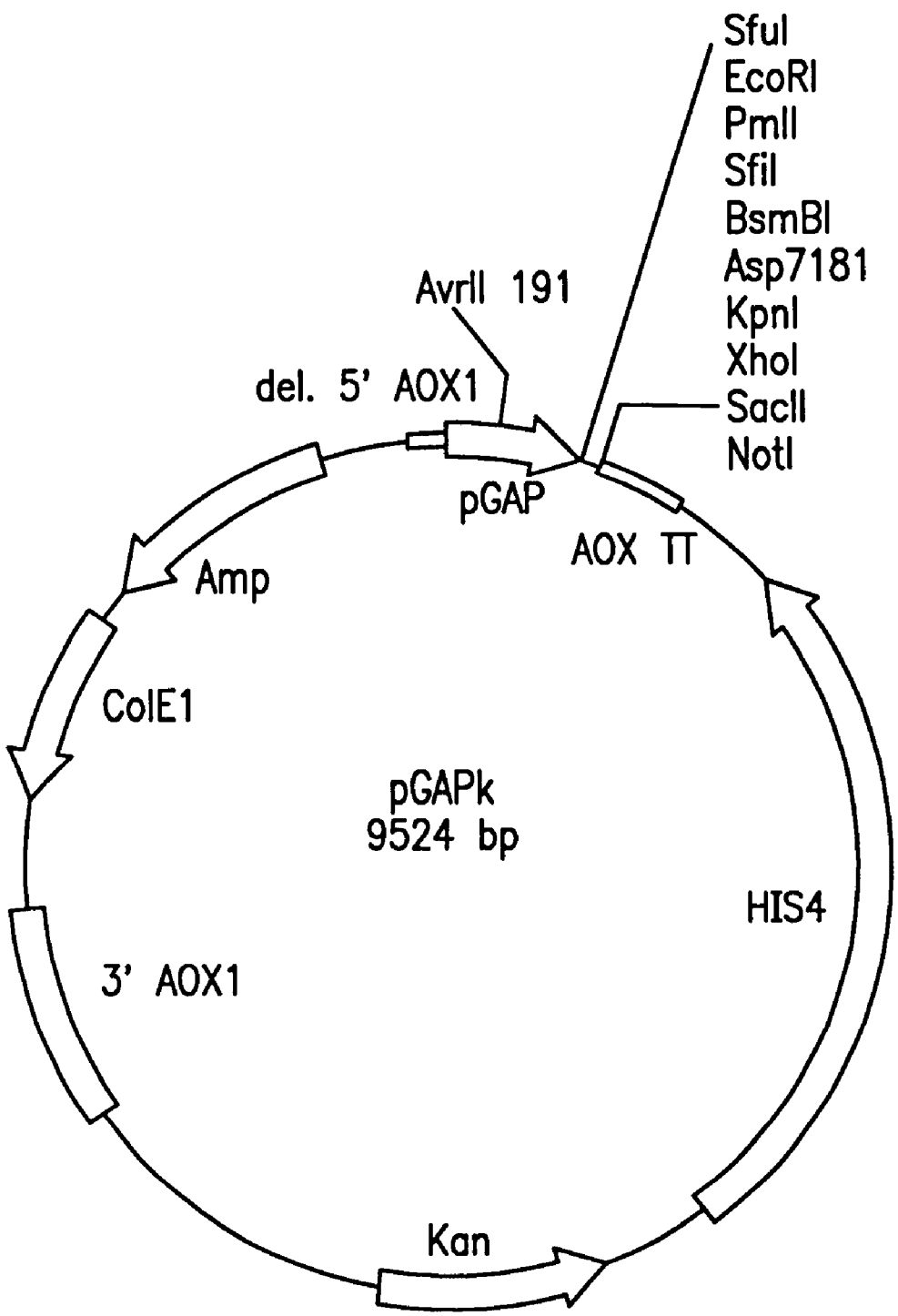
FIG. 6. Plasmid pGAPk has a 546 base pair (bp) Bgl II/NotI fragment from pGAPZ containing the GAP promoter and the Multiple Cloning Site cloned into 8980 bp BamHI/NotI fragment of pPIC9k.

Bioconversion of 5-(1,3-dioxalan-2-yl)-2-oxo-pentanoic acid to 5-(1,3-dioxolan-2-yl)-(S)-2-amino-pentanoic acid involves two enzymes—phenylalanine dehydrogenase (PDH) and formate dehydrogenase (FDH). Recombinant strain *P. pastoris* SMD1168 (pPDH9K/10) was constructed as a one-cell FDH/rPDH system, utilizing the endogenous FDH of *P. pastoris* and the cloned PDH gene of *T. intermedius*. Construction of the final recombinant vector (pPDH9K) was in two steps: a) plasmid vector pICZ-PDH was first constructed by cloning the *T. intermedius* pdh gene into plasmid vector pICZ (Invitrogen, San Diego, Calif.: FIG. 3); and, b) plasmid vector pPDH9K was then constructed by transferring the PDH gene cloned in vector pICZ-PDH into plasmid vector pIC9K (Invitrogen, San Diego, Calif.). PDH expression in this system is under the control of the AOX1 promoter with induction of expression by methanol. Expression of the PDH protein is intracellular.

Recombinant strain *P. pastoris* SMD1168 (pPDH9K/10) (ATCC 74408) was isolated in the following manner. Using the published *T. intermedius* pdh DNA sequence. DNA primers corresponding to the N-(5'CGGAATTCAAGATGCGCGACGTGTTTGAAATG3') (SEQ.ID.No.:7) and C-(5'GGGGTACCCCTCCTTGCGCTGT-TGCGGGG3') (SEQ.ID.No.:8) termini of the pdh gene were synthesized and used in a PCR reaction using *T. intermedius* target DNA. The PCR reaction yielded a single DNA fragment of expected size which was isolated, purified and digested with restriction enzymes EcoRI and KpnI. The digested PCR fragment was ligated with EcoRI/KpnI-digested plasmid vector pICZ, and the ligation mix transformed by electroporation into *P. pastoris* strain GS115. Analysis for PDH activity in cell extracts from recombinant isolate *P. pastoris* GS115 (pICZ-PDH) was positive.

Plasmid pICZ-PDH was then digested with restriction enzymes PmeI and NotI, followed by isolation and purification of the 2.5 kb DNA fragment containing the pdh gene cassette. Likewise, plasmid vector pIC9K was digested with the same two restriction enzymes and also purified. The two digested DNAs were ligated and the ligation mix transformed into *P. pastoris* strain SMD1168 using electroporation. Resulting transformants from this electroporation were then screened for resistance to high levels of the antibiotic G418 (4 mg/ml) indicating isolates containing multiple plasmid integration events. Eight high G418 resistant colonies were examined for recombinant PDH expression following methanol induction. One isolate [*P. pastoris* SMD1168 (pPDH9K/10)] demonstrated significantly higher levels of PDH activity as compared to the other transformants tested. FDH activity, as expected, was also noted in the cell extract from this isolate. Use test for the bioconversion of 5-(1,3-dioxalan-2-yl)-2-oxo pentanoic acid to 5-(1, 3-dioxalan-2-yl)-(S)-2-amino-pentanoic acid was positive using cell extracts from this isolate, either when exogenous FDH was added to the reaction mixture or when no FDH was added to the reaction mixture, demonstrating the efficacy of this one-cell FDH/rPDH system.

What is claimed is:

1. A recombinant methylotrophic yeast host cell capable of producing both phenylalanine dehydrogenase (PDH) and formate dehydrogenase (FDH) wherein said host cell comprises
   (a) recombinant nucleic acid encoding PDH, and
   (b) nucleic acid encoding FDH wherein said nucleic acid is endogenous, recombinant, or both endogenous and recombinant.

2. The recombinant host cell of claim 1 wherein the nucleic acid capable of expressing a formate dehydrogenase is endogenous.

3. The recombinant host cell of claim 1 wherein the nucleic acid capable of expressing a formate dehydrogenase is both endogenous and recombinant.

4. The recombinant host cell of claim 1 wherein said nucleic acids encoding PDH and FDH are DNA.

5. The host cell of claim 1 which is Pichia sp.

6. The host cell of claim 1 which is *Pichia pastoris*.

7. *Pichia pastoris* ATCC 74408.

8. *Pichia pastoris* ATCC 74433.

9. The host cell of claim 1 wherein said recombinant nucleic acid encoding formate dehydrogenase is from *Candida boidinii*.

10. The host cell of claim 1 wherein said recombinant nucleic acid encoding phenylalanine dehydrogenase is from a bacterium.

11. The host cell of claim 10 wherein said recombinant nucleic acid encoding phenylalanine dehydrogenase is from *Thermoactinomyces intermedius*.

12. The host cell of claim 11 wherein said *Thermoactinomyces intermedius* is ATCC 33205.

13. A composition comprising:
   (a) a recombinant bacterial host cell containing recombinant nucleic acid from *Thermoactinomyces intermedius* capable of expressing phenylalanine dehydrogenase, wherein said recombinant bacterial host cell is ATCC 98374, and
   (b) a source of formate dehydrogenase.

14. *Escherichia coli* ATCC 98374.

* * * * *

SEQUENCE LISTING

<160> NUMBER OF SEQ ID NOS: 8

<210> SEQ ID NO 1
<211> LENGTH: 31
<212> TYPE: DNA
<213> ORGANISM: Candida boidinii

<400> SEQUENCE: 1
ggaattccat atgaagatcg ttttagtctt a             31

<210> SEQ ID NO 2
<211> LENGTH: 30
<212> TYPE: DNA
<213> ORGANISM: Candida boidinii

<400> SEQUENCE: 2
ccttaagaat aataaagaat agacaaatgg               30

<210> SEQ ID NO 3
<211> LENGTH: 32
<212> TYPE: DNA
<213> ORGANISM: Thermoactinomyces intermedius

<400> SEQUENCE: 3
cggaattcaa gatgcgcgac gtgtttgaaa tg            32

<210> SEQ ID NO 4
<211> LENGTH: 29
<212> TYPE: DNA
<213> ORGANISM: Thermoactinomyces intermedius -continued

```
<400> SEQUENCE: 4
cgttctcgcg ttcctccatt gagctcgcc                                          29

<210> SEQ ID NO 5
<211> LENGTH: 31
<212> TYPE: DNA
<213> ORGANISM: Thermoactinomyces intermedius

<400> SEQUENCE: 5
catgccatgg tcgacgtgtt tgaaatgatg g                                       31

<210> SEQ ID NO 6
<211> LENGTH: 29
<212> TYPE: DNA
<213> ORGANISM: Thermoactinomyces intermedius

<400> SEQUENCE: 6
ccgctcgagt tacctccttg cgctgttgc                                          29

<210> SEQ ID NO 7
<211> LENGTH: 32
<212> TYPE: DNA
<213> ORGANISM: Thermoactinomyces intermedius

<400> SEQUENCE: 7
cggaattcaa gatgcgcgac gtgtttgaaa tg                                      32

<210> SEQ ID NO 8
<211> LENGTH: 29
<212> TYPE: DNA
<213> ORGANISM: Thermoactinomyces intermedius

<400> SEQUENCE: 8
ggggtacccc tccttgcgct gttgcgggg                                          29
```